(12) United States Patent
Hayasaki

(10) Patent No.: US 11,162,957 B2
(45) Date of Patent: Nov. 2, 2021

(54) BLOOD ANALYZING METHOD FOR D DIMER (DD) CONTENT

(71) Applicant: Sysmex Corporation, Kobe (JP)

(72) Inventor: Junki Hayasaki, Kobe (JP)

(73) Assignee: Sysmex Corporation, Hyogo (JP)

(*) Notice: Subject to any disclaimer, the term of this patent is extended or adjusted under 35 U.S.C. 154(b) by 683 days.

(21) Appl. No.: 15/622,702

(22) Filed: Jun. 14, 2017

(65) Prior Publication Data

US 2017/0363651 A1 Dec. 21, 2017

(30) Foreign Application Priority Data

Jun. 17, 2016 (JP) .............................. JP2016-121111

(51) Int. Cl.
*G01N 33/86* (2006.01)
*G01N 33/96* (2006.01)
(Continued)

(52) U.S. Cl.
CPC ........... *G01N 33/86* (2013.01); *G01N 21/272* (2013.01); *G01N 21/49* (2013.01); *G01N 21/59* (2013.01);
(Continued)

(58) Field of Classification Search
CPC ......... G01N 2001/2893; G01N 21/274; G01N 21/278; G01N 35/00693;
(Continued)

(56) References Cited

U.S. PATENT DOCUMENTS 6,277,584 B1 8/2001 Chu et al.
6,432,657 B1* 8/2002 Kikuchi ................ G01N 33/86
435/13

(Continued)

FOREIGN PATENT DOCUMENTS

JP 2006-234675 A 9/2006
JP 2012-26975 A 2/2012
(Continued)

OTHER PUBLICATIONS

Sysmex Operator's Manual Automated Blood Coagulation Analyzer (American Edition). Sysmex Corporation Kobe, Japan (Year: 2009).*

(Continued)

*Primary Examiner* — Christopher Adam Hixson
*Assistant Examiner* — Michelle Adams
(74) *Attorney, Agent, or Firm* — Crowell & Moring LLP

(57) ABSTRACT

A blood analyzing method includes optically measuring a first calibration sample prepared from a fibrin/fibrinogen degradation product (FDP) measurement reagent and a first calibrator containing D-dimer (DD) and having a first value relating to the ratio of the content of FDP to the content of DD, acquiring first calculation data based on temporal change of optical information of the first calibration measurement sample, performing optical measurement of a second calibration measurement sample prepared from FDP measurement reagent and a second calibrator containing DD and having a second value that is different from the first value, acquiring second calculated data based on a temporal change in optical information of the second calibration measurement sample, and acquiring calibration curve information indicating the relationship between the calculation data and the value relating to the amount of DD.

4 Claims, 12 Drawing Sheets

(51) Int. Cl.
| | |
|---|---|
| *G01N 21/82* | (2006.01) |
| *G01N 35/00* | (2006.01) |
| *G01N 21/27* | (2006.01) |
| *G01N 21/49* | (2006.01) |
| *G01N 21/59* | (2006.01) |
| *G01N 33/49* | (2006.01) |

(52) U.S. Cl.
CPC ............ *G01N 21/82* (2013.01); *G01N 33/49* (2013.01); *G01N 33/96* (2013.01); *G01N 35/00693* (2013.01); *G01N 2021/5969* (2013.01); *G01N 2021/825* (2013.01); *G01N 2035/00702* (2013.01); *G01N 2201/127* (2013.01); *G01N 2333/75* (2013.01); *G01N 2800/224* (2013.01)

(58) Field of Classification Search
CPC ......... G01N 2035/00702; G01N 33/86; G01N 33/96; G01N 2201/127; G01N 2201/13; G01N 2333/75; G01N 2800/224
See application file for complete search history.

(56) References Cited

U.S. PATENT DOCUMENTS

| | | | | |
|---|---|---|---|---|
| 10,209,262 | B2* | 2/2019 | Hayasaki | ............... G01N 21/82 |
| 2010/0248269 | A1 | 9/2010 | Small-Howard | |
| 2012/0028370 | A1 | 2/2012 | Nagai et al. | |
| 2013/0011869 | A1 | 1/2013 | Nagahama et al. | |
| 2013/0143243 | A1 | 6/2013 | Kobayashi et al. | |
| 2017/0059593 | A1* | 3/2017 | Hayasaki | ............... G01N 21/82 |

FOREIGN PATENT DOCUMENTS

| | | |
|---|---|---|
| JP | 2017-44668 A | 3/2017 |
| WO | 2011/125875 A1 | 10/2011 |
| WO | 2012/014996 A1 | 2/2012 |

OTHER PUBLICATIONS

Longstaff, C. et al. "Harmonisation of D-dimer—A call for action," Thrombosis Research 137 (2016) 219-220. Available online Nov. 22, 2015. (Year: 2015).*

Nobuo Okumura et al. "Comparison and Evaluation of Three FDP Values Determined by an Automated Latex Photometric Immunoassay System Using Anti-Fibrinogen, Anti-Fibrinogen-E Domain, or Anti-Neoantigen of Fibrinogen-D Domain Antibody," Japanese Journal of Clinical Chemistry, vol. 24 No. 1, p. 25-31 (Year: 1995).*

Findlay, J. et al., "Appropriate Calibration Curve Fitting in Ligand Binding Assays", *The AAPS Journal*, vol. 9, No. 2, Article 29, 2007, pp. E260-E267.

Kogan, A. et al., "Monoclonal Antibodies With Equal Specificity to D-Dimer and High-Molecular-Weight Fibrin Degradation Products", *Blood Coagulation and Fibrinolysis*, vol. 27, 2016, pp. 542-550.

Madoiwa, S. et al., "Distinct Reactivity of the Commercially Available Monoclonal Antibodies of D-Dimer and Plasma FDP Testing to the Molecular Variants of Fibrin Degradation Products", *Thrombosis Research*, vol. 132, 2013, pp. 457-464.

The Chinese Office Action dated Mar. 20, 2019 in a counterpart Chinese patent application No. 201710213083.6.

The Communication pursuant to Article 94(3) EPC dated Aug. 8, 2019 in a counterpart European patent application No. 17175990.5.

K. Fukutake, "The way for standardization on FDP/D dimer", Thrombus Hemostasis Magazine, Dec. 15, 2016, pp. 653-658, vol. 27, No. 6; Cited in the Japanese Office Action dated Jan. 7, 2020 in a counterpart Japanese patent application.

H. Tanaka et al., "Characterization of three kinds of FDP and D dimer reagents, and comparison of FDP/D dimer ratio measured by these reagents", Japanese Journal of Medical Technology, Oct. 25, 2007, pp. 1324-1329, vol. 56, No. 10; Cited in the Japanese Office Action dated Jan. 7, 2020 in a counterpart Japanese patent application.

Y. Magari et al., "Usefulness of Factor Auto D-dimer newly developed for standardization", Journal of Analytical Bio-Science, 2006, pp. 321-328, vol. 29, No. 4; Cited in the Japanese Office Action dated Jan. 7, 2020 in a counterpart Japanese patent application.

H. Sunaga, "Characteristics of Nanopia® D-dimer", Journal of Analytical Bio-Science, 2006, pp. 329-334, vol. 29, No. 4; Cited in the Japanese Office Action dated Jan. 7, 2020 in a counterpart Japanese patent application.

The Japanese Office Action dated Jan. 7, 2020 in a counterpart Japanese patent application No. 2016-121111.

The Communication pursuant to Article 94(3) EPC dated Oct. 26, 2020 in a counterpart European patent application No. 17175990.5.

* cited by examiner

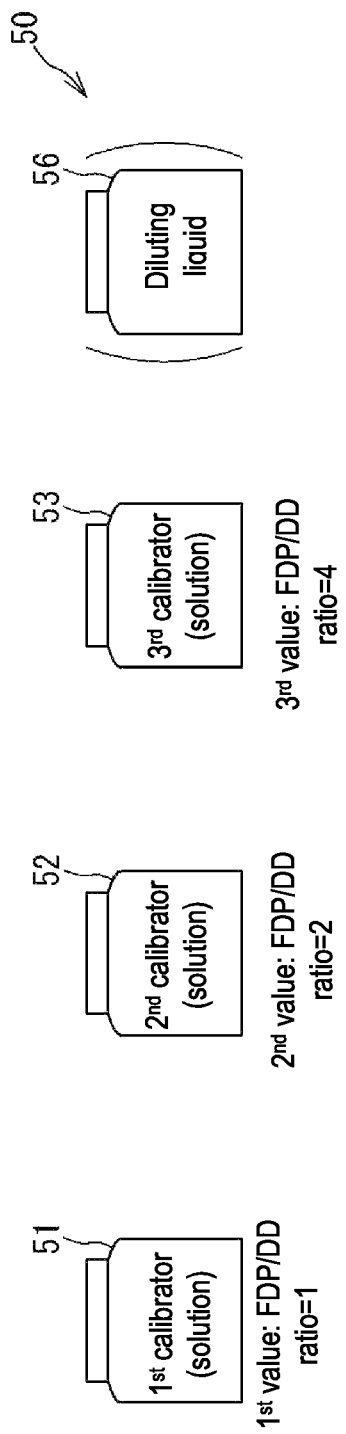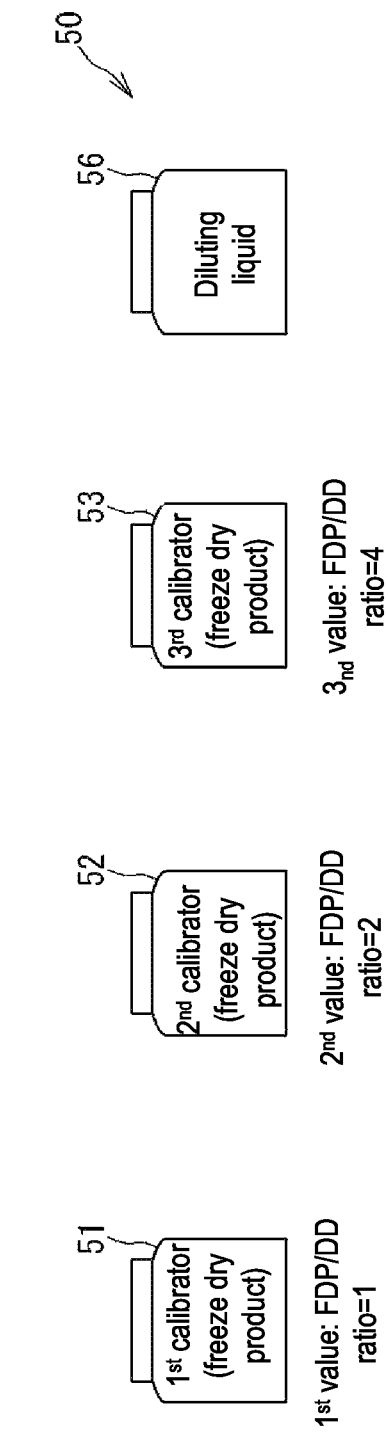

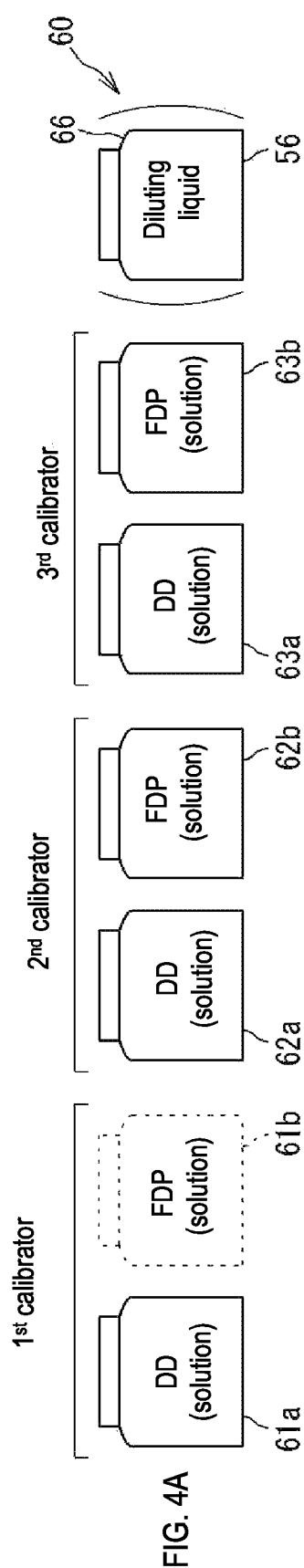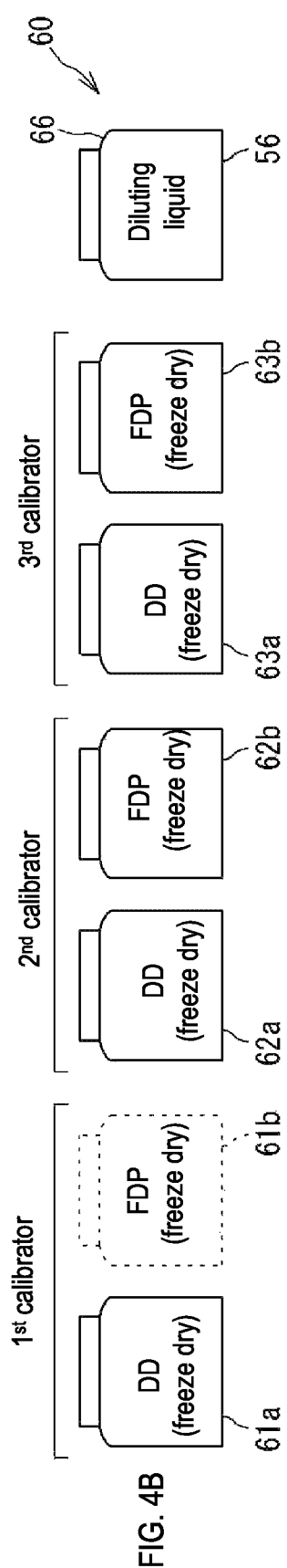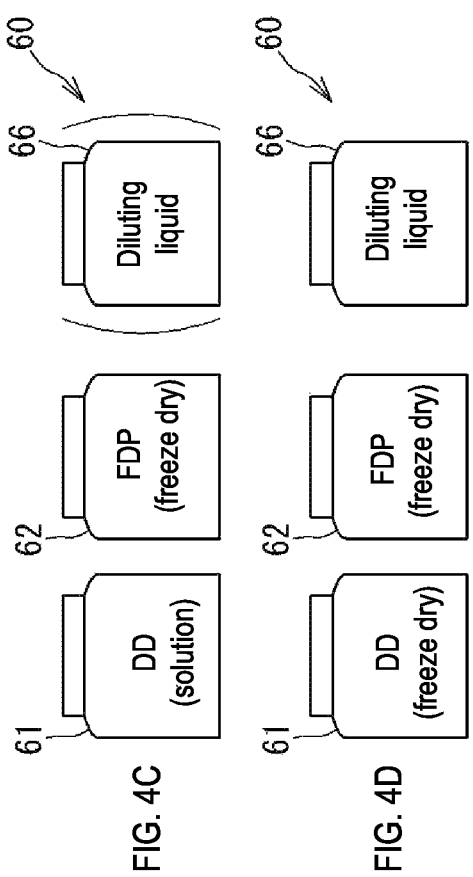

Measurement result display screen

| Date | Sample No. | Other results | FDP measured value | Fibrinolysis-enhanced flag | FDP/DD estimated value | DD estimated value |
|---|---|---|---|---|---|---|
| 16/5/6 | 00001 | | 53 μg/mL | | 2.0 | 26 μg/mL |
| 16/5/6 | 00002 | | 108 μg/mL | Enhanced fibrinolysis | 3.0 | 36 μg/mL |
| 16/5/6 | 00003 | | 34 μg/mL | | 2.0 | 17 μg/mL |
| 16/5/6 | 00004 | | 15 μg/mL | | 1.5 | 10 μg/mL |
| . . . . | . . . . | | . . . . | . . . . | . . . . | . . . . |

FIG. 12

BLOOD ANALYZING METHOD FOR D DIMER (DD) CONTENT

CROSS REFERENCE TO RELATED APPLICATIONS

This application claims priority from prior Japanese Patent Application No. 2016-121111, filed on Jun. 17, 2016, entitled "BLOOD ANALYZING METHOD, BLOOD ANALYZER, COMPUTER PROGRAM, CALIBRATOR SET, AND CALIBRATOR SET MANUFACTURING METHOD", the entire content of which is incorporated herein by reference.

FIELD OF THE INVENTION

The invention relates to a blood analyzing method and the like.

BACKGROUND

Fibrin/fibrinogen degradation product (FDP) concentration may be measured for blood analysis. The FDP may be a fibrin degradation product, a fibrinogen degradation product, and also may contain both a fibrin degradation product and a fibrinogen degradation product. D-dimer (DD) concentration also may be measured for blood analysis. DD is one type of fibrin degradation product. FDP concentration and DD concentration are used, for example, for the determination of fibrinolytic disseminated intravascular coagulation syndrome (DIC).

As shown in U.S. Patent Application Publication No. 2013/0143243 and U.S. Patent Application Publication No. 2012/0028370, FDP measurement is performed using FDP measurement reagent and DD measurement is performed using DD measurement reagent. Different reagents are used for FDP measurement and DD measurement. Therefore, these measurements are performed separately, and the measurement work becomes complicated.

Depending on the inspection facility, there may be instances where FDP measurement is performed, but DD measurement is not performed.

Therefore, it would be advantageous if it were possible to obtain a value for the amount of DD by FDP measurement.

SUMMARY OF THE INVENTION

The scope of the present invention is defined solely by the appended claims, and is not affected to any degree by the statements within this summary.

One aspect of the invention is a blood analyzing method. In an embodiment, the method comprises performing an optical measurement on a first calibration measurement sample. The first calibration measurement sample is prepared from a first calibrator and a reagent for measuring fibrin/fibrinogen degradation products (FDP). The first calibrator contains D-dimer (DD). The first calibrator has a first value related to the ratio between the content of FDP and the content of DD. The value relating the ratio of the content of FDP to the content of DD may be, for example, an FDP/DD ratio obtained by dividing the FDP content by the DD content, or an FDP/DD ratio obtained by dividing the DD content by the FDP content. The content may be indicated, for example, as a mass or as a concentration.

In the embodiment, the method includes calculating first calculation data. The first calculation data are data based on the temporal change of the optical information. The optical information is obtained by optical measurement of a first calibration measurement sample.

In the embodiment, the method includes performing an optical measurement on a second calibration measurement sample. The second calibration measurement sample is prepared from a second calibrator and a FDP measurement reagent. The second calibrator contains DD. The second calibrator has a second value that is different from the first value related to the ratio between the content of FDP and the content of DD. In the embodiment, the method includes obtaining second calculation data. The second calculation data are data based on the temporal change of the optical information. The optical information is obtained by optical measurement of a second calibration measurement sample. Performing the optical measurement on the second calibration measurement sample may be accomplished after acquiring the first calculation data or may be performed before the acquiring the first calculation data. Performing the optical measurement on the measurement sample for the second calibration may be performed after the optical measurement is performed on the measurement sample for the first calibration or may be performed before.

In the embodiment, the calibration curve information indicates the relationship between the calculation data of the calibration measurement sample and the value related to the amount of DD. The calibration curve information is acquired based on the first calculation data, the second calculation data, the first value, and the second value. The calibration curve information is information that functions as a calibration curve, such as information indicating a mathematical formula corresponding to a line representing the relation between the calculation data and a value related to the amount of DD, or information indicating the value of a coefficient of the mathematical formula. The calibration curve information need not be data of a drawn line indicating the relationship between the calculation data and the value related to the amount of DD.

Here, the "value related to the amount of DD" may be a value related to the DD itself, such as the DD concentration or the DD mass, or a value calculated from a value related to the DD itself and a value related to an object other than the DD, for example, it also may be a value related to the ratio between the FDP content and the DD content. In a first calibrator and a second calibrator, the FDP concentration may be known or unknown. Even if the FDP concentration is unknown, it can be obtained by measuring the calibration measurement sample prepared using the FDP measurement reagent.

The "value related to the amount of DD" in the acquired calibration curve information is sufficient if it meets the definition of "the value related to the amount of DD" as described above, and need not be a value of the same dimension as the first value and the second value. For example, the first value and the second value are FDP/DD ratios, and the "value related to the amount of DD" in the acquired information may be the DD concentration. The DD concentration is, for example, a dimension value expressed in units of µg/mL, whereas the FDP/DD ratio is a dimensionless value, and the dimensions of both are different. The FDP concentration also may be known or may be obtained by measurement with respect to a measurement sample for calibration as described above.

Another aspect of the present invention is a blood analyzer including a measurement part for performing optical measurement on a measurement sample and a processing part for executing a process.

In the embodiment, the measurement part performs optical measurement on the first calibration measurement sample prepared from an FDP measurement reagent and a first calibrator which contains D-dimer (DD) and has a first value relating to the ratio of fibrin/fibrinogen degradation product (FDP) content to DD content. The measurement part optically measures a second calibration measurement sample prepared from FDP measurement reagent and a second calibrator which contains DD and has a second value that is different from the first value related to the ratio between the FDP content and the DD content. In the embodiment, the processing executed by the processing part includes acquiring the first calculation data, acquiring the second calculation data, and acquiring the calibration curve information. The blood analyzer may further include a storage part for storing the calibration curve information. The blood analyzer can analyze blood using the calibration curve information stored in the storage part.

Yet another aspect of the invention is a computer program to perform a computer-executable process.

In the embodiment, the process executed by computer includes having the measurement part performing optical measurement on the first calibration measurement sample prepared from an FDP measurement reagent and a first calibrator which contains D-dimer (DD) and has a first value relating to the ratio of fibrin/fibrinogen degradation product (FDP) content to DD content. The process executed by computer may include having the measurement part optically measuring a second calibration measurement sample prepared from FDP measurement reagent and a second calibrator which contains DD and has a second value that is different from the first value related to the ratio between the FDP content and the DD content. The process executed by computer may include acquiring first calculation data based on a temporal change in optical information obtained by optical measurement of the first calibration measurement sample. The process executed by computer may include acquiring second calculation data based on a temporal change in optical information obtained by optical measurement of the second calibration measurement sample. The process executed by computer may include acquiring calibration curve information indicating a relationship between the calculation data and a value related to the amount of DD based on the first calculation data, the second calculation data, the first value, and the second value. The process executed by computer may further include storing the calibration curve information in the storage part. The process executed by the computer may further include analyzing the blood using the calibration curve information stored in the storage part.

Another aspect of the invention is a calibrator set for obtaining a relationship between calculation data of a measurement sample used for calibration and a value relating to the amount of DD, and includes a first calibrator and a second calibrator.

In the embodiment, the first calibrator contains a D-dimer (DD), and has a value related to the ratio of fibrin/fibrinogen degradation product (FDP) content to DD content that is the first value, and is used to prepare the first calibration measurement sample together with fibrin/fibrinogen degradation product (FDP) measurement reagent. A second calibrator contains DD and has a second value that is different from the first value related to the ratio between the FDP content and the DD content, and is used for the preparation of a second calibration measurement sample together with FDP measurement reagent. The first calibrator and the second calibrator may be a solution or a dry product.

Another aspect of the invention is a method for manufacturing a calibrator set for obtaining calibration curve information. In the embodiment, the manufacturing method includes preparing a first calibrator that includes D-dimer (DD) so that the ratio of fibrin/fibrinogen degradation product (FDP) to D-dimer (DD) is a first value. The manufacturing method includes preparing a second calibrator containing DD so that the ratio between the content of FDP and the content of DD is a second value different from the first value. At least one of the first calibrator and the second calibrator contains FDP other than DD. The first calibrator is used for preparation of a first calibration measurement sample by being mixed with an FDP measurement reagent. The second calibrator is used for preparation of a second calibration measurement sample by being mixed with an FDP measurement reagent. The first calibration measurement sample and the second calibration measurement sample are used to acquire calibration curve information showing the relationship between a value related to the amount of DD and calculation data based on a temporal change in optical information obtained by optical measurement of a calibration measurement sample.

Another aspect of the invention is a method of using a calibrator set. In an embodiment, the method of use includes a calibration process for acquiring calibration curve information based on first calculation data indicating a temporal change in optical information obtained by optical measurement of the first calibration measurement sample, second calculation data based on a temporal change in optical information obtained by optical measurement of the second calibration measurement sample, a first value, and a second value.

Another aspect of the invention is a calibrator preparation kit for obtaining a relationship between the amount of DD and calculation data of a calibration measurement sample, and includes a first D-dimer (DD), a second DD, and an FDP other than DD.

In an embodiment, the first DD is DD of a first amount used to prepare a first calibrator to be used for preparing a first calibration measurement sample together with a fibrin/fibrinogen degradation product (FDP). The second DD is DD of a second amount used to prepare a second calibrator to be used for preparing a second calibration measurement sample together with the FDP measurement reagent. FDP other than DD is, for example, a fibrinogen degradation product. FDP other than DD is mixed with at least one of the first DD and the second DD. The first DD and the second DD may be a solution or a dry product.

Another aspect of the invention is a method of using a calibrator preparation kit. In an embodiment, the method of use includes a calibrator preparation step and a calibration step. The calibrator manufacturing step includes preparing a first calibrator using the first DD, and preparing a second calibrator using a second DD. At least one of the preparation of the first calibrator using the first DD and the preparation of the second calibrator using the second DD includes mixing an FDP other than DD and the first DD or the second DD. The calibration step includes acquiring calibration curve information based on first calculation data indicating a temporal change in optical information obtained by optical measurement of the first calibration measurement sample prepared from the first calibrator, second calculation data based on a temporal change in optical information obtained by optical measurement of the second calibration measurement sample prepared from the second calibrator, a first value, and a second value.

According to the invention, it is possible to obtain a value relating to the amount of DD by FDP measurement.

BRIEF DESCRIPTION OF THE DRAWINGS

FIGS. 3A and 3B are schematic diagrams of a calibrator set;
FIGS. 4A-4D are schematic diagrams of a calibrator preparation kit;
FIG. 12 is a diagram showing a result display screen.

DETAILED DESCRIPTION OF THE PREFERRED EMBODIMENTS

1. Calibration Outline

Figure 1:
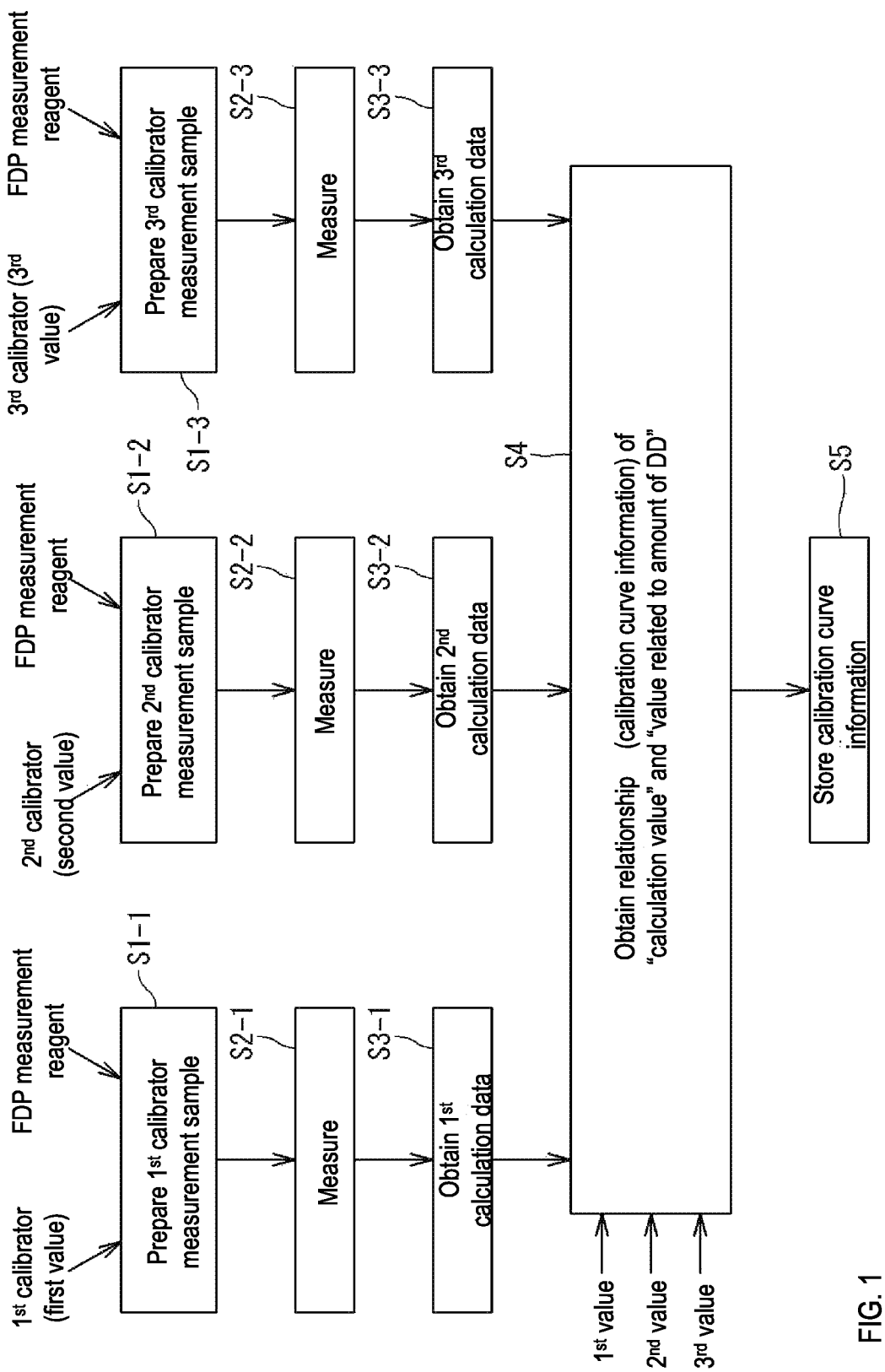
FIG. 1 is a flow chart of the calibration step.

The method of the embodiment includes the calibration step shown in FIG. 1. In the calibration step of the embodiment, calibration curve information for obtaining an estimate value of the value related to the amount of DD is acquired from calculation data obtained by FDP measurement of FDP in the sample.

The calibration curve information shows the relationship between the calculation data calculated from the measurement result of the FDP measurement on the measurement sample and the value related to the amount of DD of the measurement sample. The value related to the amount of DD of the measurement sample is, for example, the DD concentration of the sample or a value related to the ratio of the FDP content to the DD content. Once the calculation data is obtained based on the FDP measurement of the measurement sample, the estimated value of the DD amount of the measurement sample can be obtained using the calibration curve information.

In general, in the case of calibration for FDP measurement, a value related to FDP is measured using a calibrator in which a value related to FDP is set to a predetermined value, and in the case of calibration for DD measurement, a value related to the amount of DD is measured using a calibrator in which a value related to the amount of DD is set to a predetermined value. On the other hand, the calibration step of the embodiment is a calibration for FDP measurement, but a calibrator is used in which the value relating to the ratio between the FDP content and the DD content is set to a predetermined value.

Generally, to obtain a value related to the amount of DD, such as the DD concentration or the FDP/DD ratio, DD measurement to measure DD in the sample is required. However, by using the calibration curve information of the embodiment, it is possible to obtain an estimated value of the amount of DD by FDP measurement.

The calibration step of the embodiment includes the sample preparation step shown as Steps S1-1, S1-2, S1-3. In the sample preparation step, a calibration measurement sample is prepared from the calibrator and the FDP measurement reagent. A plurality of calibrators are used in the embodiment. The plurality of calibrators are, for example, three calibrators including a first calibrator, a second calibrator, and a third calibrator. In step S1-1, a first calibration measurement sample is prepared from the first calibrator, a second calibration measurement sample is prepared from the second calibrator in step S1-2, and a third calibration measurement sample is prepared the third calibrator in step S1-3.

Note that steps S1-1, S1-2, S1-3 may be performed in parallel or sequentially. When performed sequentially, the order is discretionary. The same applies to steps S2-1, 2-2, S2-3, S3-1, S3-2, S3-3.

The FDP measurement reagent is a reagent used for FDP measurement. In the embodiment, the FDP measurement reagent is used for preparing a measurement sample for calibration from a calibrator. The FDP measurement reagent also is used for preparing a measurement sample for analysis from a blood sample as described later. Various commercially available products can be used as FDP measurement reagents, for example, FDP measurement kit/Rias Auto P-FDP reagent manufactured by Sysmex Corporation, or Elpia FDP-P reagent manufactured by LSI Medience Corporation, can be used.

In steps S2-1, S2-2, and S2-3, each calibration measurement sample is measured. These measurements are FDP measurements. Measurement of a sample is performed by optical measurement. Optical information is obtained by the optical measurements. Optical measurement will be described later.

In steps S3-1, S3-2, S3-3, calculation data calculated based on the FDP measurement result are acquired. In step S3-1, first calculation data are obtained on the basis of measurement of the first calibration measurement sample, in step S3-2 second calculation data are obtained on the basis of measurement of the second calibration measurement sample, and in step S3-3 the third calculation data are obtained based on the measurement of the third calibration measurement sample. Each calculated data is calculated based on the temporal change of the optical information. The optical information is, for example, optical density (OD).

In step S4, calibration curve information is acquired from a plurality of calculation data and values relating to the amount of DD of the calibrator. The calibration curve information is generated using a plurality of calculation data acquired in steps S3-1, S3-2, and S3-3. A value related to the amount of DD of the calibrator also is used for the generation of the calibration curve information.

The acquired calibration curve information is stored in the storage part 32 of the blood analyzer 10. The calibration curve information stored in the storage part 32 is used for obtaining an estimated value of the amount of DD from calculation data obtained by FDP measurement performed on the analysis measurement sample, for example. Blood analyzer 10 will be described later.

2. Calibrator

Figure 2:
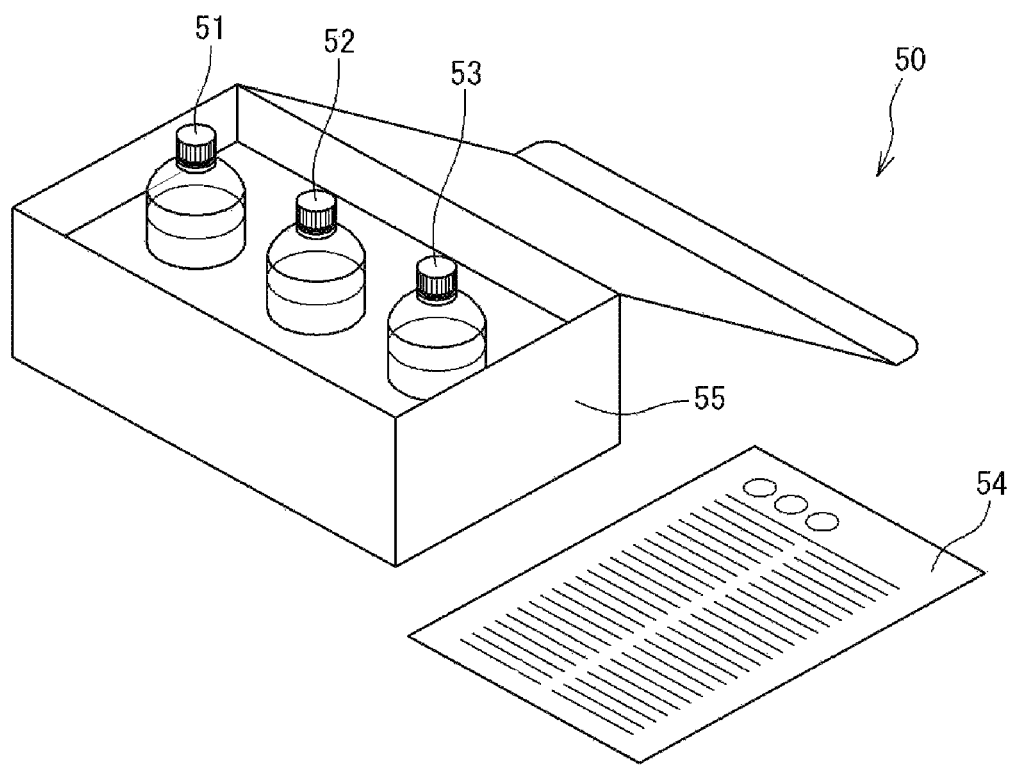
FIG. 2 is a perspective view of the calibrator set.

FIG. 2 shows a calibrator set 50 according to the embodiment. The calibrator set 50 is used to acquire the calibration curve information and is the object of FDP measurement. The calibrator set 50 includes a first calibrator, a second calibrator, and a third calibrator. The number of calibrators included in the calibrator set 50 may be 2 or more, but from the viewpoint of obtaining more appropriate calibration curve information, there are preferably 3 or more calibrators. The first calibrator is housed in the first container 51, the second calibrator is housed in the second container 52, and the third calibrator is housed in the third container 53. The containers 51, 52, 53 are stored in the packing box 55.

The calibrator set 50 has a package insert 54. The package insert 54 describes how to use the calibrator set. The description of the package insert 54 includes, for example, an explanation that each calibrator included in the calibrator set 50 is to be used for the calibration process shown in FIG. 1.

Each calibrator included in the calibrator set 50 has a value related to the ratio between the FDP content and the DD content adjusted to a predetermined value. In each calibrator of the embodiment, the FDP concentration is also known in addition to the known FDP/DD ratio. Note that when the FDP concentration and the FDP/DD ratio are known, the DD concentration is also substantially known.

The calibrator is, for example, a solution having at least DD. For example, the calibrator of the embodiment is prepared by mixing an artificial DD, an artificial fibrinogen degradation product and a dilution liquid. Artificial DD is prepared, for example, by mixing fibrinogen, calcium, thrombin, and factor XIII to prepare a fibrin clot, and then degrading it with plasmin. Artificial fibrinogen degradation products are produced, for example, by degrading fibrinogen with plasmin. For example, a fibrinolytic diluent liquid manufactured by Sysmex Corporation is used as a dilution liquid. For example, water such as purified water or physiological saline also may be used instead of or in addition to such a dilution liquid. Although the calibrator of the embodiment does not include fibrin degradation product other than DD, it may contain fibrin degradation product other than DD, such as E fraction of fibrin degradation product.

Each calibrator of the embodiment is prepared by mixing an artificial DD, an artificial fibrinogen degradation product and a solvent, and is adjusted, for example, to the FDP concentration and the FDP/DD ratio shown in the following Table 1.

TABLE 1

| | FDP Concentration (μg/mL) | Amount FDP/ Amount D-dimer | D-dimer and FDP ratio |
|---|---|---|---|
| $1^{st}$ calibrator | 39.9 | 1 | D-dimer: 1 FDP: 0 |
| $2^{nd}$ calibrator | 41.5 | 2 | D-dimer: 1 FDP: 1 |
| $3^{rd}$ calibrator | 41.9 | 4 | D-dimer: 1 FDP: 3 |

As shown in Table 1, the FDP/DD ratio of each calibrator is a different value. In Table 1, the FDP/DD ratio (first value) of the first calibrator is 1, the FDP/DD ratio (second value) of the second calibrator is 2, the FDP/DD ratio of the third calibrator (3 value) is 4.

In the first calibrator, the amount of fibrinogen degradation product is 0 when the amount of DD is 1. That is, the first calibrator is an FDP consisting only of DD, and does not contain fibrinogen degradation product. In the second calibrator, the amount of fibrinogen degradation product is 1 when the amount of DD is 1. In the third calibrator, the amount of fibrinogen degradation product is 3 when the amount of DD is 1.

The FDP/DD ratio of each calibrator shown in Table 1 is an example, and although not particularly limited, from the viewpoint of obtaining appropriate calibration curve information for analyzing a blood specimen, the FDP/DD ratio of each calibrator is preferably 1 or more to 16 or less. The FDP/DD ratio of each calibrator is more preferably 8 or less, and even more preferably 5 or less. The FDP/DD ratio of each calibrator is more preferably 2 or more, and even more preferably 3 or more. Blood analysis using calibration curve information is an analysis for diagnosis in which a value related to the amount of DD is used for diagnosis of a disease condition, for example, analysis for disseminated intravascular coagulation syndrome (DIC), analysis for deep venous thrombosis (DVT), or analysis for pulmonary embolism (PE). Analysis for DIC includes analysis for fibrinolysis-enhanced DIC. In the determination for diagnosis of the pathophysiology of fibrinolysis-enhanced DIC, the FDP/DD ratio or DD/FDP ratio is used as one of the thresholds for judgment. For example, when the FDP/DD ratio of a blood sample exceeds a reference value of the FDP/DD ratio, which is a threshold value for determination, it may be determined as fibrinolysis-enhanced DIC.

At least one of the plurality of calibrators included in the calibrator set 50 preferably has an FDP/DD ratio at a value equal to the reference value of the FDP/DD ratio or a value close to the reference value used as a threshold for blood analysis in which the calibration curve information is used. For example, at least one of the plurality of calibrators for obtaining the calibration curve information used for determining the fibrinolysis-enhanced DIC preferably has a value equal to or a value near the reference value of the FDP/DD ratio for determination of the fibrinolysis-enhanced DIC. A calibrator having an FDP/DD ratio reference value or an FDP/DD ratio in the vicinity thereof is effective for obtaining more appropriate calibration curve information. Here, a value near the reference value of the FDP/DD ratio is a value in the range of ±0.5 of the FDP/DD ratio reference value.

For example, if the FDP/DD ratio reference value is 2, the calibrator set 50 preferably includes a calibrator whose FDP/DD ratio is in the range of 1.5 to 2.5, and calibrator set 50 more preferably includes a calibrator whose FDP/DD ratio is 2. If the FDP/DD ratio reference value is 4, the calibrator set 50 preferably includes a calibrator having an FDP/DD ratio in the range of 3.5 to 4.5, and the calibrator set 50 more preferably includes a calibrator having an FDP/DD ratio of 4. If the FDP/DD ratio reference value is 8, the calibrator set 50 preferably includes a calibrator having an FDP/DD ratio in the range of 7.5 to 8.5, and the calibrator set 50 more preferably includes a calibrator having an FDP/DD ratio of 8. When a value in the range of 2 to 8 is used as the reference value of the FDP/DD ratio for the determination of fibrinolysis-enhanced DIC, the calibrator set preferably includes calibrators having FDP/DD ratios in the range of 1.5 to 8.5. When a value in the range of 3 to 5 is used as a reference value of the FDP/DD ratio for determination of the fibrinolysis-enhanced DIC, the calibrator set 50 preferably includes calibrators having FDP/DD ratios in the range of 2.5 to 5.5.

The calibrator set 50 has a calibrator with an FDP/DD ratio (high value FDP/DD ratio) larger than the FDP/DD ratio reference value and a calibrator with an FDP/DD ratio (low value FDP/DD ratio) smaller than the FDP/DD ratio reference value. Such a calibrator set 50 is effective for obtaining more appropriate calibration curve information for condition determination. If the FDP/DD ratio reference value is 2, for example, the high value FDP/DD ratio can be 4 and the low value FDP/DD ratio can be 1. If the FDP/DD ratio reference value is 4, for example, the high value FDP/DD ratio can be set to 8 and the low value FDP/DD ratio can be set to 1.

The calibrator set 50 preferably includes a calibrator with a high value FDP/DD ratio, a calibrator with a low value FDP/DD ratio, an FDP/DD ratio between the high value FDP/DD ratio and the low value FDP/DD ratio (intermediate value FDP/DD Ratio) calibrator. If the FDP/DD ratio reference value is 2, for example, the high value FDP/DD ratio can be 4, the low value FDP/DD ratio can be 1, and the intermediate value FDP/DD ratio can be 2 or 3. If the FDP/DD ratio reference value is 4, for example, the high value FDP/DD ratio can be 8, the low value FDP/DD ratio can be 1, and the intermediate value FDP/DD ratio can be 4. Although the intermediate value FDP/DD ratio may be different from the FDP/DD ratio reference value, it is preferably the same.

As shown in Table 1, the FDP concentration of each calibrator was adjusted to 39.9 μg/mL for the first calibrator, 41.5 μg/mL for the second calibrator, 41.9 μg/mL for the third calibrator. From Table 1, the DD concentration of each calibrator is 39.9 μg/mL for the first calibrator, 20.75 μg/mL for the second calibrator, and 10.475 μg/mL for the third calibrator.

Although the FDP concentration of each calibrator shown in Table 1 is an example and is not particularly limited, from the viewpoint of obtaining appropriate calibration curve information for blood sample analysis, the FDP concentration of each calibrator is 1 μg/mL or more to 120 μg/ML or less. When the FDP concentration is within this range, it becomes a calibrator having an appropriate FDP concentration in view of reference values for determination of various disease states. From a clinical point of view, the FDP concentration is more preferably 5 μg/mL or more, and still more preferably 40 μg/mL. From a clinical point of view, the FDP concentration of the calibrator is more preferably 80 μg/mL or less. Blood analysis in which calibration curve information is utilized includes analysis for fibrinolysis-enhanced DIC as described above. The FDP concentration is used as another threshold for determination in determining fibrinolysis-enhanced DIC. When the FDP concentration of the blood sample exceeds the reference value of the FDP concentration which is the threshold for determination, it may be judged to be a fibrinolysis-enhanced DIC. For example, 40 μg/mL, 50 μg/mL, or 80 μg/mL is used as a reference value of the FDP concentration for determination of fibrinolysis-enhanced DIC.

The plurality of calibrators included in the calibrator set 50 preferably have an FDP concentration value equal to or a value close to the reference value of the FDP concentration which is a threshold value used for blood analysis in which the calibration curve information is used. In this way, the calibration curve information becomes more appropriate in the concentration range of the FDP concentration reference value or the vicinity thereof, which is advantageous for blood analysis. Here, a value near the reference value of the FDP concentration is a value in the range of ±15% of the reference value of the FDP concentration.

For example, when blood analysis using calibration curve information is an analysis for fibrinolysis-enhanced DIC and the reference value of FDP concentration for fibrinolysis-enhanced DIC determination is only 40 μg/mL, each of the plurality of calibrators included in the calibrator set 50 preferably has an FDP concentration of 40 μg/mL or a value close thereto (34 μg/mL to 46 μg/mL). In the case of Table 1, the FDP concentrations of the three calibrators are invariably close to 40 μg/mL, which is the reference value of FDP concentration.

The FDP concentrations of the plurality of calibrators included in the calibrator set 50 need not all correspond to a single FDP concentration reference value. For example, the FDP concentration of a first group consisting of a plurality of calibrators may be equal to or close to a first FDP concentration reference value, and a second group of FDP concentrations consisting of another plurality of calibrators may be a value equal to or close to a second FDP concentration reference value which is different from the first FDP concentration reference value. Three or more FDP concentration reference values may be used. By having a plurality of FDP concentration reference values, the calibration curve information becomes more appropriate for a plurality of reference values of FDP concentration. For example, the calibrator set 50 can have six calibrators shown in Table 2.

TABLE 2

|  | FDP Concentration (μg/mL) | Amount FDP/ Amount D-dimer | D-dimer and FDP ratio |
|---|---|---|---|
| $1^{st}$ calibrator | 39.9 | 1 | D-dimer: 1 FDP: 0 |
| $2^{nd}$ calibrator | 41.5 | 2 | D-dimer: 1 FDP: 1 |
| $3^{rd}$ calibrator | 41.9 | 4 | D-dimer: 1 FDP: 3 |
| $4^{th}$ calibrator | 79.5 | 1 | D-dimer: 1 FDP: 0 |
| $5^{th}$ calibrator | 80.3 | 2 | D-dimer: 1 FDP: 1 |
| $6^{th}$ calibrator | 81.1 | 4 | D-dimer: 1 FDP: 3 |

In Table 2, the first calibrator, the second calibrator, and the third calibrator belong to a first group, the fourth calibrator, the fifth calibrator, and the sixth calibrator belong to a second group. The FDP concentrations of the calibrators of the first group correspond to a first FDP concentration reference value of 40 μg/mL, and the FDP concentrations of the calibrators of the second group correspond to a second FDP concentration standard value of 80 μg/mL.

As shown in FIG. 3A, each calibrator included in the calibrator set 50 may be in the form of a solution in which the FDP/DD ratio and FDP concentration are adjusted as shown in Table 1, and also may be in the form of a dry product such as a lyophilized product, as shown in FIG. 3B. A calibrator which is a dry product can be obtained, for example, by lyophilizing each calibrator prepared as a solution. The dry product calibrator has the FDP/DD ratio or the DD mass adjusted to a known value.

Dry product calibrator also is contained in containers 51, 52, 53. The calibrator set 50 in which the calibrator is a dry product preferably contains a solvent of a calibrator which is a dry product. The solvent is, for example, purified water, physiological saline, or dilution liquid. The solvent is contained in the fourth container 56. The fourth container also is stored in the packing box 55. The solvent also is used to adjust the calibrator to a given FDP concentration.

A package insert 54 of the calibrator set 50 that includes dry product calibrators describes a method for preparing a solution calibrator from a solvent and a dry product calibrator. By preparing a solution calibrator according to the package insert 54, for example, a calibrator that has an FDP/DD ratio and FDP concentration as shown in Table 1 is obtained. The package insert 54 also includes an explanation that the solution calibrator should be used for the calibration process shown in FIG. 1.

Note that the calibrator set 50 shown in FIG. 3A in which the calibrator is a solution may also include a dilution liquid similarly to the calibrator set 50 in FIG. 3B. It is possible to prepare a calibrator with another FDP concentration range by diluting each calibrator with a dilution liquid.

FIG. 4 shows a calibrator preparation kit 60. The calibrator preparation kit 60 is a kit for preparing the calibrator set 50. The calibrator set 50 prepared from the calibrator preparation kit 60 also is an object of FDP measurement used for acquiring the aforementioned calibration curve information similarly to the calibrator set 50 in FIGS. 3A and 3B. In the embodiment, it is assumed that a first calibrator, a second calibrator, and a third calibrator having an FDP/DD ratio and an FDP concentration substantially similar to those in Table 1 are prepared from the calibrator preparation kit 60.

The calibrator preparation kit 60 shown in FIG. 4A includes an artificial DD for artificial DD and artificial fibrinogen degradation product for preparing the first calibrator, an artificial DD and fibrinogen degradation product for preparing the second calibrator, and artificial DD fibrinogen degradation product for preparing the third calibrator. The artificial DD for preparing the first calibrator is housed in the first container 61a, and the artificial fibrinogen degradation product for preparing the first calibrator is contained in the second container 61b. The artificial DD for preparing the second calibrator is contained in the third container 62a, and the artificial fibrinogen degradation product for producing the second calibrator is contained in the fourth container 62b. The artificial DD for preparing the third calibrator is contained in the fifth container 63a, and the artificial fibrinogen degradation product for producing the third calibrator is contained in the sixth container 63b.

The containers 61a, 61b, 62a, 62b, 63a, and 63b are stored in a packing box. Artificial DD and artificial fibrinogen degradation product contained in containers 61a, 61b, 62a, 62b, 63a, 63b are in the form of a solution. Since a fibrinogen degradation product is unnecessary in the first calibrator of Table 1, artificial fibrinogen degradation product contained in the second container 61b can be omitted.

The amount of DD stored in the first container 61a, the third container 62a, and the fifth container 63a is known. In FIG. 4A, since the artificial DD is a solution, the known amount of DD is represented, for example, by the concentration [μg/mL]. The amount of artificial fibrinogen degradation product contained in the second container 61b, the fourth container 62b, and the sixth container 63b is known. In FIG. 4A, since artificial fibrinogen degradation products are solutions, the amount of known artificial fibrinogen degradation products is expressed, for example, as concentration [μg/mL].

For example, artificial DD having a DD concentration of 40 μg/mL is contained in the first container 61a of FIG. 4A. The artificial DD contained in the first container 61a can be used as is as a first calibrator having an FDP concentration of 40 μg/mL and an FDP/DD ratio of 1.

For example, an artificial DD with a DD concentration of 40 μg/mL is contained in the third container 62a in FIG. 4A, and artificial fibrinogen degradation product with a fibrinogen degradation product concentration of 40 μg/mL is contained in the fourth container 62b. A second calibrator having an FDP concentration of 40/μg/mL and FDP/DD ratio of 2 is prepared by mixing the artificial DD of the third container 62a and the artificial fibrinogen degradation product of the fourth container 62b at a volume ratio of 1:1.

Note that since the concentrations of DD of the first container 61a and the third container 62a are the same, either one may be omitted.

For example, artificial DD with a DD concentration of 20 μg/mL is contained in the fifth container 63a of FIG. 4A, and in the sixth container 63b, for example, contains artificial fibrinogen degradation product at a concentration of 60 μg/mL. A third calibrator having an FDP concentration of 40/μg/mL and FDP/DD ratio of 4 is prepared by mixing the artificial DD of the fifth container 63a and the artificial fibrinogen degradation product of the sixth container 63b at a volume ratio of 1:1.

The calibrator preparation kit 60 of FIG. 4A also has a package insert 54. The package insert 54 describes the calibrator preparation step for preparing a calibrator from artificial DD and artificial fibrinogen degradation product. The package insert 54 also includes an explanation that the prepared calibrator should be used for the calibration process shown in FIG. 1.

As shown in FIG. 4B, at least one of DD and fibrinogen degradation product contained in each container of the calibrator preparation kit 60 may be in the form of a dry product such as a lyophilized product. Dry product type DD or fibrinogen degradation product can be obtained, for example, by lyophilizing DD or fibrinogen degradation products prepared as a solution. The mass of DD or FDP in each container is adjusted to a known value. It is preferable that the calibrator preparation kit 60 of FIG. 4B contains a solvent of dry product DD or fibrinogen degradation product. The solvent is, for example, purified water, physiological saline, or dilution liquid. The solvent is contained in the seventh container 66. The seventh container 66 also is stored in a packing box. The solvent also is used to adjust the calibrator to a given FDP concentration.

Note that the calibrator preparation kit 60 shown in FIG. 4A may also contain a dilution liquid similarly to the calibrator preparation kit 60 of FIG. 4B. It is possible to prepare a calibrator with another FDP concentration range by diluting the prepared calibrator with a dilution liquid.

The calibrator preparation kit 60 of FIG. 4B also has a package insert 54. The package insert 54 describes the calibrator preparation step for preparing a calibrator from dry product artificial DD, artificial fibrinogen degradation product, and solvent. The package insert 54 also includes an explanation that the prepared calibrator should be used for the calibration process shown in FIG. 1.

The calibrator preparation kit 60 shown in FIG. 4C includes an artificial DD of the solution type and artificial fibrinogen degradation product of the solution type. The artificial DD is housed in the first container 61 and the artificial fibrinogen degradation product is contained in the second container 62. The containers 61 and 62, are stored in a packing box.

The artificial DD of the first container 61 has a known DD concentration, and the artificial fibrinogen degradation product of the second container 62 has a known fibrinogen degradation product concentration. For example, an artificial DD with a DD concentration of 40 μg/mL is contained in the first container 61, and artificial fibrinogen degradation product with a fibrinogen degradation product concentration of 40 μg/mL is contained in the second container 62.

The artificial DD contained in the first container 61 can be used as it is as a first calibrator having an FDP concentration of 40 μg/mL and an FDP/DD ratio of 1.

A second calibrator having an FDP concentration of 40/μg/mL and FDP/DD ratio of 2 is prepared by mixing the artificial DD of the first container 61 and the artificial fibrinogen degradation product of the second container 62 at a volume ratio of 1:1.

A third calibrator having an FDP concentration of 40/μg/mL and FDP/DD ratio of 4 is prepared by mixing the artificial DD of the first container 61 and the artificial fibrinogen degradation product of the second container 62 at a volume ratio of 1:3.

The calibrator preparation kit 60 of FIG. 4C also has a package insert 54. The package insert 54 describes the calibrator preparation step for preparing a calibrator from artificial DD and artificial fibrinogen degradation product. The package insert 54 also includes an explanation that the prepared calibrator should be used for the calibration process shown in FIG. 1.

As shown in FIG. 4D, at least one of DD and fibrinogen degradation product contained in each container of the calibrator preparation kit 60 may be in the form of a dry product such as a lyophilized product. Dry product type DD or fibrinogen degradation product can be obtained, for example, by lyophilizing DD or fibrinogen degradation products prepared as a solution. The mass of DD or FDP in each container is adjusted to a known value. It is preferable that the calibrator preparation kit 60 of FIG. 4D contains a solvent of dry product DD or fibrinogen degradation product. The solvent is, for example, purified water, physiological saline, or dilution liquid. The solvent is contained in the third container 66. The third container 66 also is stored in a packing box. The solvent also is used to adjust the calibrator to a given FDP concentration.

Note that the calibrator preparation kit 60 shown in FIG. 4C may also contain a dilution liquid similarly to the calibrator preparation kit 60 of FIG. 4D. It is possible to prepare a calibrator with another FDP concentration range by diluting the prepared calibrator with a dilution liquid.

3. Blood Analyzer

Figure 5:
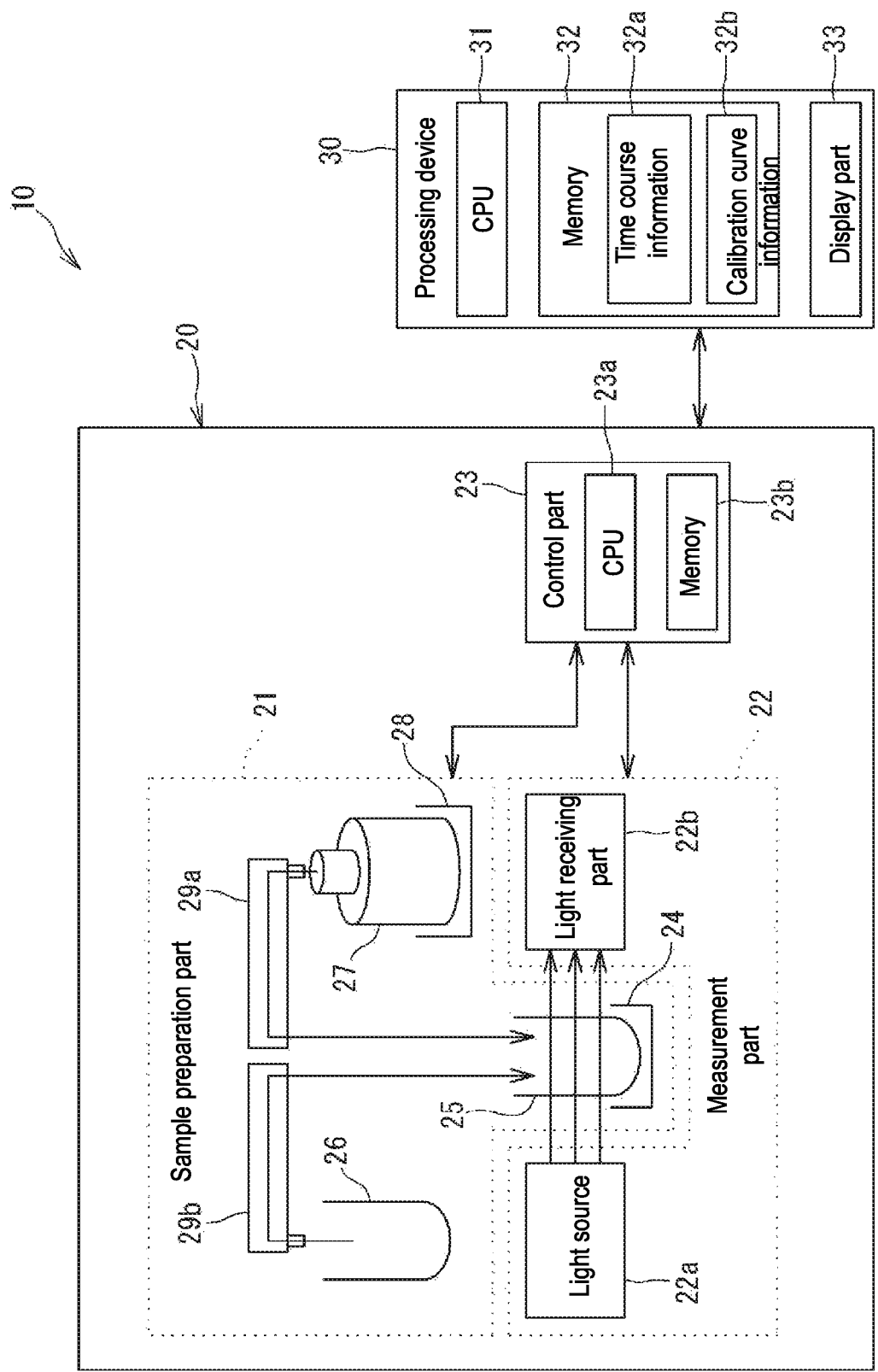
FIG. 5 is a structural view of a blood analyzer.

FIG. 5 shows a blood analyzer 10 used in the blood analysis process. The blood analyzer 10 executes steps S11 to S14 shown in FIG. 6. The blood analyzer 10 of the embodiment measures blood samples taken from a subject by immunoturbidimetry or the like and analyzes blood samples. The blood sample to be analyzed is, for example, plasma. The blood sample also may be serum or whole blood. The blood analyzer 10 also is used for the calibration process of FIG. 1.

The blood analyzer 10 includes a measurement device 20 and a processing device 30. The measurement device 20 measures a measurement sample including a blood sample. The processing device 30 analyzes the measurement result acquired from the measurement device 20.

The measurement device 20 includes a sample preparation part 21, a measurement part 22, and a control part 23. The sample preparation part 21 includes a cuvette holding unit 24, a reagent setting unit 28, a reagent dispensing unit 29*a*, and a sample dispensing unit 29*b*. The cuvette holding unit 24 holds a cuvette 25. The cuvette 25 is a container for the preparation of the measurement sample. A calibration measurement sample prepared from a calibrator is also prepared in the cuvette 25, in addition to preparing a measurement sample for analysis prepared from a blood sample.

A reagent container 27 containing the reagent is set in the reagent setting part 28. The reagent contained in the reagent container 27 includes a reagent for FDP measurement. The reagent dispensing unit 29*a* suctions the reagent from the reagent container 27 set in the reagent setting part 28 and dispenses the reagent to the cuvette 25. The sample dispensing unit 29*b* suctions the blood sample or the calibrator from the sample container 26 and dispenses the blood sample or the calibrator to the cuvette 25. Note that the sample container 26 is conveyed to a sample suctioning position by the sample dispensing unit 29*b* by a conveying device (not shown).

Figure 6:
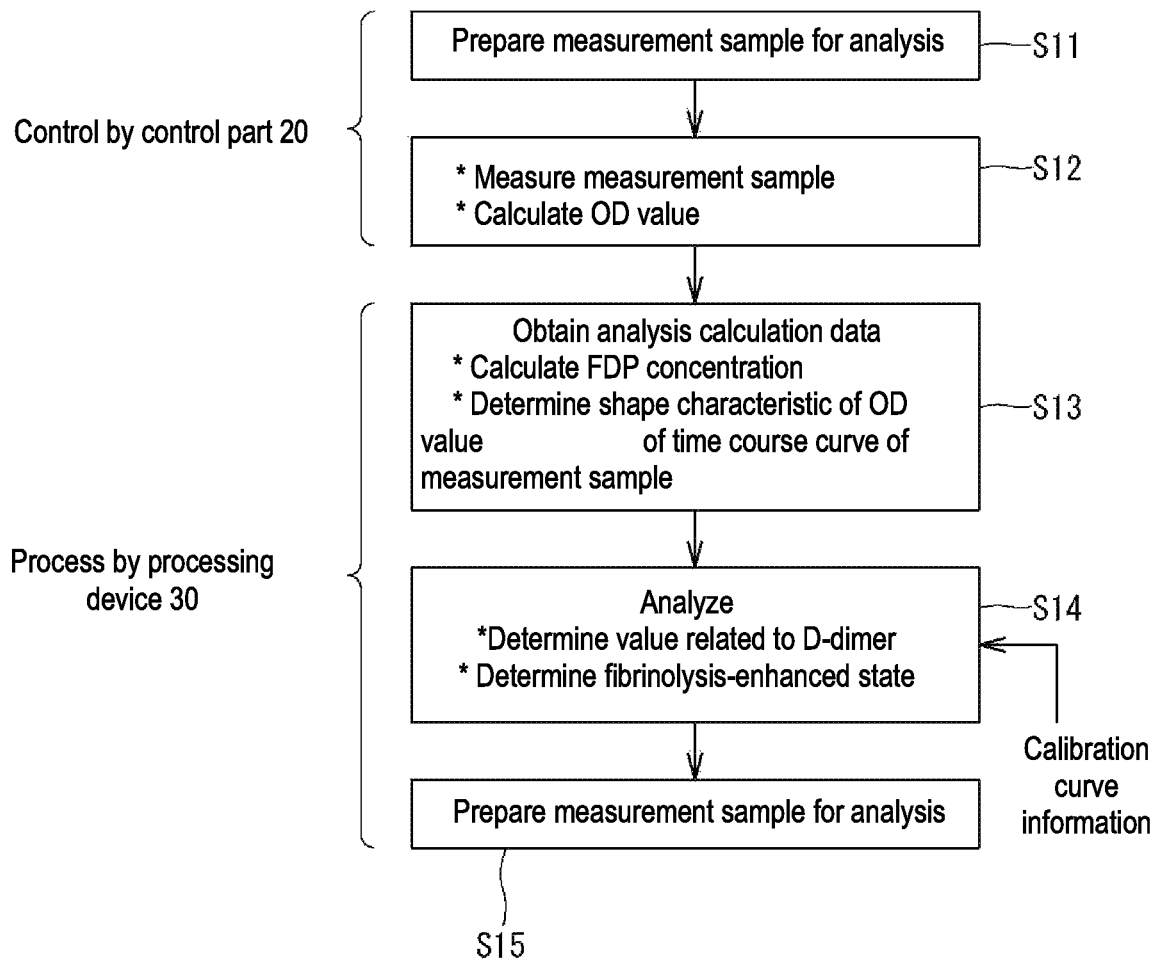
FIG. 6 is a flow chart of a sample analysis process step.

In step S11 of FIG. 6, the sample preparation unit 21 mixes the blood sample dispensed in the cuvette 25 and the reagent, and prepares an analysis measurement sample for FDP measurement. The operation for preparing samples by the measurement sample preparing part 21 is controlled by the control part 23. The sample preparation part 21 performs steps S1-1, S1-2, S1-3 of FIG. 1 in the same manner as step S11 to prepare a measurement sample for calibration.

The measurement part 22 is configured to include a light source 22*a* and a light receiving part 22*b*. The light source 22*a* is provided to irradiate light on the measurement sample in the cuvette 25. The light source 22*a* is configured to include a halogen lamp or LED. The wavelength of the light irradiated from the light source 22*a* may be a wavelength suitable for measurement, for example, 800 nm, 575 nm, or 730 nm. The light source 22*a* is controlled by the control part 23. The control part 23 operates the measurement part 22 according to measurement instructions from the processing device 30.

The light receiving part 22*b* receives transmitted light or scattered light from the measurement sample, and outputs detection signals, which are electrical signal corresponding to the amount of light received, as measurement results. The light receiving part 22*b* is configured, for example, to include a photodiode.

In step S12 of FIG. 6, the measurement part 22 measures the turbidity of the measurement sample and outputs a detection signal indicating the change over time of the turbidity of the measurement sample. The detection signal may be a signal indicating a change over time of scattered light or transmitted light transmitted through the measurement sample. For example, when turbidity of a measurement sample is measured by an immunoturbidimetric method, the light receiving part 22*b* receives the light transmitted through the measurement sample irradiated from the light source 22*a*. When the agglutination reaction of the immunocomplex proceeds in the measurement sample, the amount of transmitted light is reduced and the output level of the electric signals decreases over time because the turbidity of the measurement sample increases. Therefore, the detection signal output from the light receiving part 22*b* indicates the change over time of the turbidity of the measurement sample. As in step S12, the measurement part 22 performs steps S2-1, S2-2, and S2-3 of FIG. 1 to measure the calibration measurement sample.

The control part 23 receives the detection signals from the measurement part 22, and calculates optical information based on the detection signals. The control part 23 functions as an acquisition part that acquires optical information. The optical information is, for example, an optical density (OD) value. The OD value is calculated based on the rate of increase in turbidity indicated by the detection signals. The OD value, for example, may be calculated from transmitted light intensity, rather than turbidity. The control unit 23 calculates the time series data of the OD value during the period from the measurement start to the measurement completion based on the detection signal during the period from the start of measurement to the completion of measurement. The time series data of the OD value are data showing the change over time of the OD value, that is, the change of the OD value that appears with the passage of time, and shows the time course curve of the optical information of the measurement sample. The control part 23 transmits the time series data of the calculated OD value to the processing device 30.

The control part 23 includes a CPU 23*a* and memory (storage part) 23*b*. The control part 23 functions as the control part 23 by causing the CPU 23*a* to execute a computer program stored in the memory 23*b*.

The processing device 30 includes a CPU 31, a memory (storage part) 32, and a display part 33. The processing device 30 functions as the processing device 30 by causing the CPU 31 to execute a computer program stored in the memory 32.

The processing device 30 causes the measurement part 22 to perform optical measurement of the measurement sample. The processing device 30 transmits a measurement instruction for the control part 23 to the control part 23 so as to cause the measurement part 22 to perform optical measurement. The processing device 30 receives the time series data of the OD value which is the measurement result of the optical measurement from the control part 23. In step S13 of FIG. 6, the processing device 30 acquires the analysis calculation data from the OD value time series data. The analytical measurement data includes first data and second data. The first data show the concentration of FDP which is the original measurement object in the FDP measurement.

The second data are information (hereinafter referred to as "time course characteristic") indicating the shape characteristic of the time course curve showing the temporal change of the optical information. The time course characteristic is obtained by executing a process of analyzing the shape of the time course curve by the CPU 31 of the processing device 30. The analysis of the time course curve is performed using the time course analysis information 32a. As shown in FIG. 5, the time course analysis information 32a is stored in the memory 32.

Similar to step S13, the processing device 30 performs steps S3-1, S3-2, S3-3 in FIG. 1 to acquire the calibration calculation data. Note that the calibration calculation data only needs to include the second data indicating the time course characteristic, and may or may not include the first data indicating the FDP concentration.

In step S14, the processing device 30 analyzes the sample based on the analysis calculation data. The analysis includes obtaining a value (estimated value) related to the amount of DD of the blood sample based on the second data showing the time course characteristic. The calibration curve information acquired in the calibration process is used to determine the value related to the amount of DD of the blood sample. As shown in FIG. 5, the calibration curve information 32b is stored in the memory 3. 2 The value related to the amount of DD of the blood sample, for example, is an estimate of DD concentration or an estimate of FDP/DD ratio.

The analysis in step S14 includes a determination of a sample state such as a determination of a fibrinolysis-enhanced state of a blood sample. The determination of the fibrinolysis-enhanced state is made based on the FDP concentration indicated by the first data and the estimated value of the value related to the DD amount of the blood sample.

In step S15, the processing device 30 displays the result display screen on the display part 33. The result display screen can display the values related to the amount of DD, determination results of fibrinolysis-enhanced state, and other measurement results. The result display screen will be described later.

4. FDP Measurement Time Course Characteristic] (4.1 Calculation of FDP Concentration by FDP Measurement]

The processing device 30 calculates the first data indicating the FDP concentration from the time series data of the OD values indicating the time course curve of the OD value of the measurement sample. The FDP concentration is calculated according to the FDP concentration calculation procedure described in the package insert of the FDP measurement reagent used for FDP measurement. Specifically, the processing device 30 obtains the amount of change per unit time (for example, one minute) of the OD value which is optical information, applies the obtained change amount to the calibration curve for obtaining the FDP concentration, and calculates the FDP concentration in the measurement sample.

The first data indicating the FDP concentration may be information directly indicating the FDP concentration or indirectly indicating the FDP concentration such as a parameter correlating with the FDP concentration. Information directly indicating the FDP concentration, for example, is the FDP concentration calculated according to the above FDP concentration calculation procedure. Information indirectly indicating the FDP concentration, for example, is the amount of change of the OD value per predetermined time. The amount of change of the OD value per predetermined time directly shows the FDP concentration since it correlates with the FDP concentration as is clear from use for calculation of FDP concentration.

4.2 Analysis of FDP Measurement Time Course

Generally, to obtain a value related to the amount of DD, such as the DD concentration or the FDP/DD ratio, DD measurement to measure DD in the sample is required. However, the present inventors have surprisingly found that it is possible to obtain a value related to the amount of DD by FDP measurement without performing DD measurements.

More specifically, the present inventors found that there is a correlation between the time course characteristic, which is the shape characteristic of the time course curve of FDP measurement on the measurement sample, and the value related to the amount of DD of the measurement sample. That is, the shape of the time course curve of FDP measurement varies depending on the amount of DD in the measurement sample. By utilizing this correlation, it is possible to estimate the value related to the amount of DD based on the time course characteristic which is the result of FDP measurement.

Figure 7:
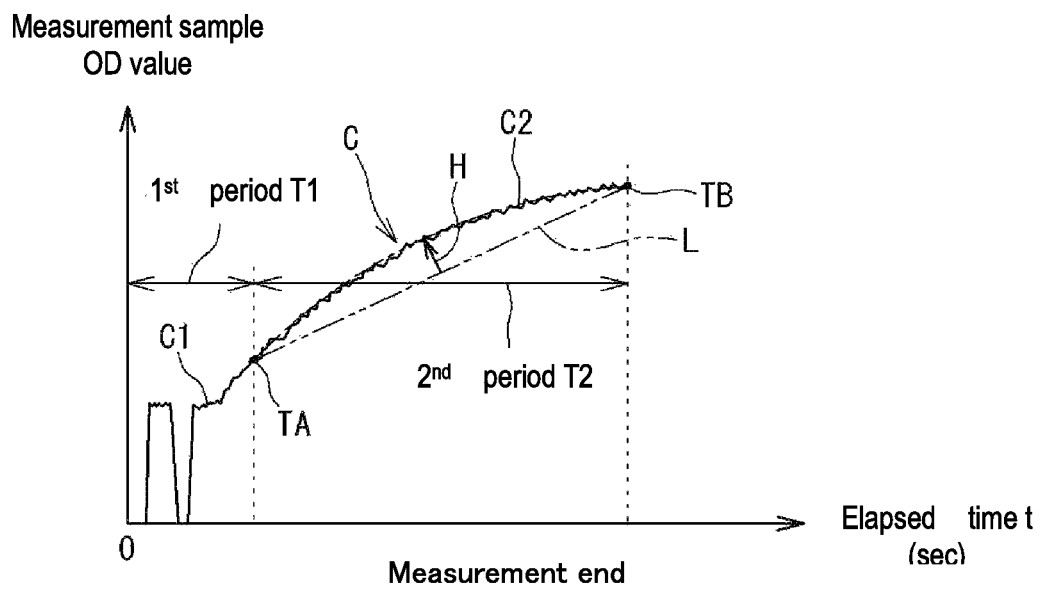
FIG. 7 shows a time course curve.

The optical information of the measurement sample is information obtained by optically measuring the measurement sample, for example, an optical density (OD) value. The time course curve of the optical information of the measurement sample is a curve showing the temporal change of the optical information of the measurement sample and is roughly the curve C as shown in FIG. 7. The time course curve is drawn based on the time series data of the OD value acquired by the processing device 30.

In FIG. 7, the horizontal axis represents the elapsed time from the start of measurement of the measurement sample, and the vertical axis represents the OD value of the measurement sample. The time course characteristic varying with the amount of DD is indicated by the degree of curvature of the time course curve. The degree of curvature of the time course curve is the degree of curvature of the time course curve of optical information that increases with time. Here, although the OD value increases while repeatedly slightly increasing and decreasing, consider the curvature of the time course curve when macroscopically examining the time course curve without considering the fluctuation of the time course curve due to weak increase and decrease.

In many cases, the time course curve of the OD value of the measurement sample includes a curve portion C1 of a first period T1 from measurement start (elapsed time=0 sec) to about several tens of seconds, and a curve portion C2 of a second period T2 from the first period T1 continuing to the end of measurement. The first period T1, for example, may be 30 seconds. Although the OD value monotonically increases in the second period T2, in the first period T1, the turbidity of the measurement sample is not stabilized, and large increases and decreases in the OD value may occur. Since such a first period T1 does not appropriately represent the change over time of the OD value, the degree of curvature can be determined with high accuracy by excluding the first period T1 when calculating the degree of curvature of the time course curve C. Note that when the OD value monotonously and stably increases even during the first period T1, the curve portion C1 in the first period T1 may be taken into consideration when calculating the degree of curvature of the time course curve C.

For example, when considering the degree of curvature of the time course curve C in the range from the start point TA to the end point TB of the second period T2 of the time course curve C in FIG. 7, as the upward projection amount H of the curve portion becomes larger in the time course curve C from the straight line L connecting the start point TA and the end point TB, the curve bends greatly, the degree of curvature increases. Conversely, the smaller the projection amount H, the smaller the degree of curvature.

In many cases, as shown in FIG. 7, the time course curve of the OD value is an upward convex curve in the second period T2, and the projection amount H is a positive value. However, in the case of a blood sample or the like collected from a subject lacking a factor for forming DD, the sample may be downward convex with respect to the straight line L, and the degree of bending and the projection amount H are negative values in this case.

The processing device 30 calculates a time course characteristic such as the degree of curvature of the time course curve from the time series data of the OD values. Time course characteristic can be indicated by various indicators.

4.3 Variation of Indicators Showing Time Course Characteristics

FIG. 8 shows a variation of the time course characteristic which changes depending on the amount of DD. A first example of the time course characteristic is the surface area of the convex area of the time course curve. As shown in FIG. 8A, the convex area surface area is calculated as the size of the region circumscribed by the time course curve and the straight line L connecting the starting point TA and the ending point TB of the area calculation target period of the surface area calculation in the time course curve C. When the start point TA to the end point TB of the calculation target period is set within a period in which the OD value of the measurement sample monotonously increases as in the second period T2 of FIG. 7, the degree of curvature is appropriately reflected on the surface area of the convex area. Note that the surface area of the area above the straight line L is treated as a positive value, and the surface area of the area below the straight line L is treated as a negative value.

The surface area of the convex area increases as the upward degree of curvature increases upward as viewed from the straight line L, and the surface area of the convex area decreases as the degree of upward curvature decreases.

The second example of the time course characteristic is the radius of curvature or the curvature of the time course curve C. A curvature or radius of curvature of an approximate curve can be the curvature or radius of curvature of the time course curve since the curvature of the approximate curve can be taken as the radius of curvature or the curvature of the time course curve. By curve approximation of the time course curve C, the time course curve can be captured macroscopically by neglecting the fluctuation of the time course curve due to weak increase and decrease.

Note that it is preferable to treat the radius of curvature or curvature as a positive value when the time course curve C has an upward convex shape, and treat the radius of curvature or curvature as a negative value in the case of a downward convex shape. When the radius of curvature or the curvature changes between the start point TA and the end point TB of the calculation target range of the radius of curvature or curvature, as shown in FIG. 8B, the average of the curvature radii or average curvature of a plurality of points P1, within the target period may be obtained as the time course characteristic.

A third example of the time course characteristic is a coefficient when the time course curve C is a polynomial approximation. For example, the coefficient a obtained by approximating the time course curve with the quadratic function of $ax^2+bx+c$ can be taken as the time course characteristic.

A fourth example of the time course characteristic is the projection amount H of the time course curve. As shown in FIG. 8C, the projection amount H extends vertically from the midpoint P of the straight line L connecting the start point TA to the end point TB of the calculation target range of the projection amount H to the time course curve C side, and is calculated as the length reaching to the time course curve C. It is preferable that the projection amount H in the case where the time course curve C is convex upward is treated as a positive value and the protrusion amount H in the case of the downward convex shape is treated as a negative value.

Figure 8A:
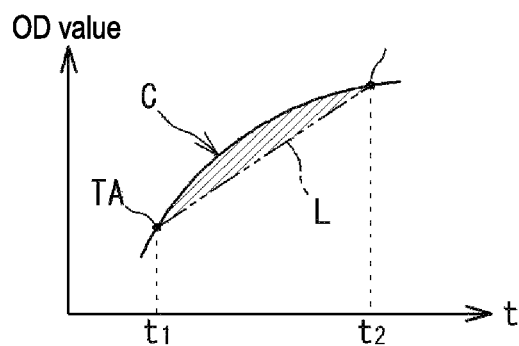
FIGS. 8A-8F are variation diagrams of indicators showing time course characteristics.
Figure 8D:
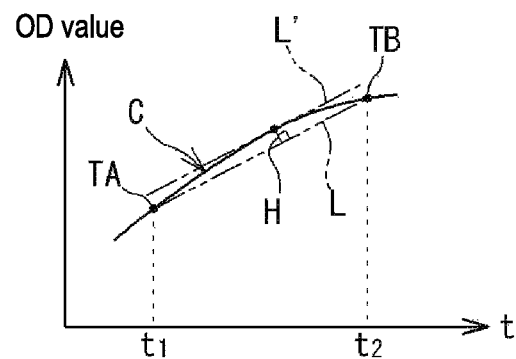
Figure 8B:
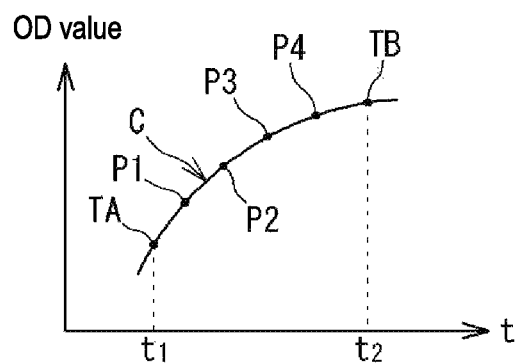

The projection amount H is a line L' that is parallel to the straight line L as shown in FIG. 8D, and also may be the interval of the straight line L and the line L' which becomes a tangent line of the time course curve C from the start point TA to the end point TB of the calculation target range of the projection amount H.

Figure 8E:
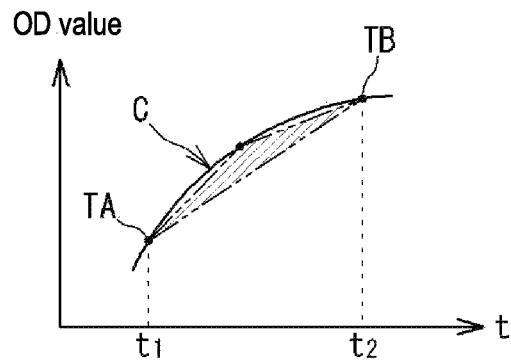
Figure 8C:
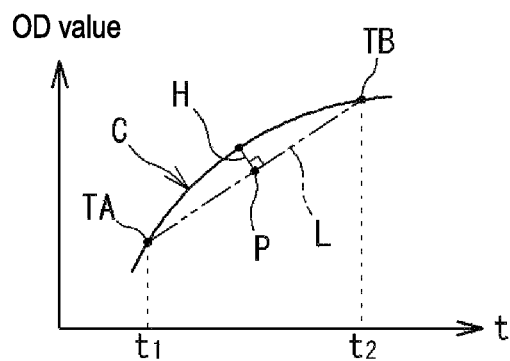

A fifth example of the time course characteristic is the surface area of the approximation figure of the convex area. The surface area of the approximation figure of the convex area is one of the variations of the information indicating the size of the surface area of the convex area in the first example. For example, as shown in FIG. 8E, the approximation figure of the convex area can be a triangle that approximates the area surrounded by the time course curve C and the straight line L from the starting point TA to the ending point TB of the target range of the area calculation. The approximation figure may be a semicircle or an arbitrary polygon.

Figure 8F:
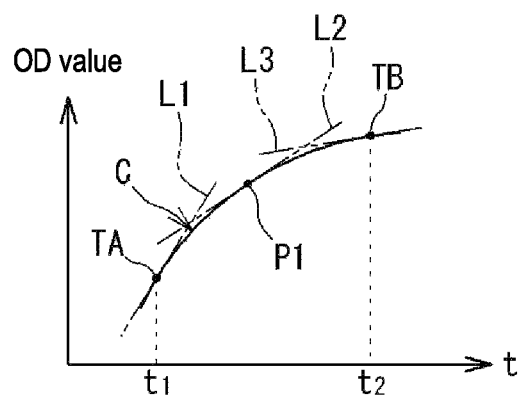

A sixth example of the time course characteristic is a discretionary two ratios among the tangent lines L1, L2, L3 of the time course curve C or the slope of the regression line. As shown in FIG. 8F, the slope of the tangent line or the regression line, for example, is calculated as the slope of the tangent line L1 or the regression line at the early stage of the time course curve (for example, the start point TA or its vicinity), the slope of the tangent line L2 or regression line at the middle stage of the time course curve (for example, the point P1 between the start point TA and the end point TB), or the slope of the tangent line L3 or the regression line at the last stage of the time course curve (for example, the end point TB or its vicinity). The ratio of the slopes of any two discretionary tangent lines L1, L2, L3 or the regression line calculated in this way can be calculated as the time course characteristic. The time course characteristic here, for example, is the slope of L1/the slope of L2, the slope of L2/the slope of L1 or the slope of L3/the slope of L1. A plurality of tangents or regression lines may be divided into two groups, and the sum or average of the slopes may be calculated for each group and the sum of the slopes or the ratio of the average of the two groups may be calculated as the time course characteristic. For example, in the first half of the time course curve, the slopes of the three tangent lines are calculated, and a first average value thereof is calculated. Similarly, in the last half of the time course curve, the slopes of the three tangent lines are calculated, and a second average value thereof is calculated. The ratio between the first average value and the second average value can be calculated as the time course characteristic.

Note that the first example to the sixth example of the time course characteristic invariably indicate the degree of curvature of the time course curve.

4.4 Convex Area Surface Area Calculation Example

In the following, the convex area surface area of the first example is adopted as the time course characteristic. The processing device 30 calculates the convex area surface area from the time series data of the OD value by using the following expression (1). Expression (1) is an example of the time course analysis information 32a, and is stored in the memory 32.

Expression 1

$$\text{Convex area surface area} = \sum_{t=30}^{150} \frac{(OD(t)) - a \times t - b}{1000} \quad (1)$$

Here, t is the time [sec] in the time course curve. OD (t) is the OD value at time t seconds. A×t−b is a regression equation of a straight line connecting the start point TA of the curvature degree calculation to the end point TB of the curvature degree calculation in the time course curve. Here, the start point TA is the OD value at the time of 30 seconds from the start of measurement (t=0), and the end point TB is the OD value at the time of 150 seconds from the start of the measurement. Note that the start point TA may be the average value of the OD values during a period near the start point reference time (for example, 30 seconds) (for example, from 27.5 to 32.5 seconds), or the end point TB may be the average value of the OD values during a period near the end point reference time (for example, 150 seconds) (for example, 147.5 to 152.5 seconds). In the case of dilution measurement, a value obtained by multiplying the surface area of the convex area calculated using the expression (1) by the dilution ratio can be taken as the surface area of the convex area.

5. Example of Calibration to Obtain Calibration Curve Information

The processing device 30 executes step 4 in FIG. 1 to acquire the calibration curve information 32b from the time course characteristics. Here, it is assumed the first calculation data of the first calibration measurement sample, the second calculation data of the second calibration measurement sample, and the third calculation sample of the third calibration measurement sample prepared from the three calibrators shown in Table 1 have been obtained. Each calculated data includes second data indicating the convex area surface area (see FIG. 8A) as the time course characteristic. FDP measurement kit/Rias Auto P-FDP reagent manufactured by Sysmex Corporation was used for preparing the measurement sample.

Prior to step S4, the first value, the second value, and the third value, which are values related to the ratio between the content of FDP and the content of DD of each calibrator, are registered in the memory 32 of the processing device 30.

Here, the first value for the first calibrator is FDP/DD ratio=1, the second value for the second calibrator is FDP/DD ratio=2, the third value for the third calibrator is FDP/DD ratio=4 (see Table 1). It also is assumed that values relating to FDP of each calibrator are registered in the memory 32 of the processing device 30. Here, the value related to FDP is the FDP concentration (see Table 1).

The value is registered by the processing device 30 receiving user input. The user refers, for example, to the FDP/DD ratio and FDP concentration described in the attached document 54 of the calibrator set 50 or the calibrator preparation kit 60, and inputs these values to the processing device 30.

The processing device 30 divides the convex area surface area by the FDP density registered in the memory 32 to obtain the convex area surface area per FDP unit concentration. Table 3 shows the convex area surface area, FDP concentration, and convex area surface area per FDP unit concentration of each calibrator.

TABLE 3

|  | Convex area surface area (mOD − sec) | FDP Concentration (µg/mL) | Convex area surface area per FDP unit concentration |
|---|---|---|---|
| 1st calibrator | 9542 | 39.9 | 239 |
| 2nd calibrator | 8624 | 41.5 | 208 |
| 3rd calibrator | 4601 | 41.9 | 110 |

Note that the FDP concentration for obtaining the convex area surface area per FDP unit concentration need not be the value registered in the memory 32 by the user's input, for example, the FDP concentration indicated by the first data obtained by FDP measurement in steps S3-1, S3-2, S3-3 in FIG. 1 can be used.

Figure 9:
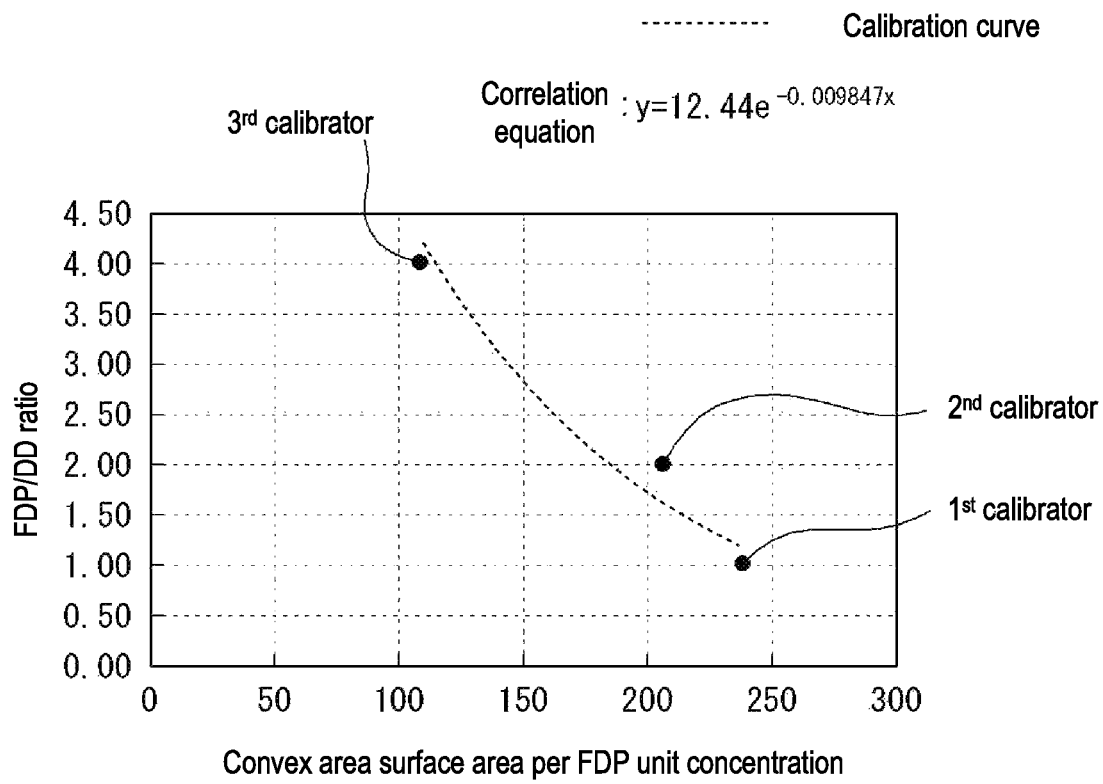
FIG. 9 is a calibration curve based on analysis information obtained in a calibration step.

The processing device 30 generates the calibration curve information 32b from the convex area surface area per FDP unit concentration of each calibrator and the FDP/DD ratio of each calibrator registered in the memory 32. FIG. 9 shows a calibration curve indicated by the calibration curve information 32b. In FIG. 9, the horizontal axis represents the convex area surface area per FDP unit concentration and the vertical axis represents the FDP/DD ratio. The first calibrator, second calibrator, and third calibrator are plotted in FIG. 9. An approximation curve for each plotted point of each calibrator becomes a calibration curve. The approximation curve is represented, for example, by an exponential function. The calibration curve is a correlation formula of the convex area surface area per FDP unit concentration and the FDP/DD ratio. The correlation equation obtained from the first calibrator, the second calibrator, and the third calibrator is as shown in the following expression (2).

Expression 2

$$FDP/D\text{-dimer ratio} = 12.44 e^{(-0.009847x)} \quad (2)$$

x: Convex area surface area per FDP unit concentration

Expression (2) obtained by the calibration process is stored in the memory 32 as calibration curve information 32b.

The calibration curve information 32b of expression (2) is information for obtaining the FDP/DD ratio, but the calibration curve information 32b may be information for obtaining the DD concentration.

The calibration curve information 32b for determining the DD concentration is generated from the convex area surface area per FDP unit concentration of each calibrator and the DD concentration of each calibrator. The DD concentration in this case may be the DD concentration previously registered in the memory 32 for each calibrator or the DD concentration calculated from the FDP concentration obtained by FDP measurement. Calculation of the DD concentration can be calculated based on the FDP concentration obtained by FDP measurement and the FDP/DD ratio previously registered in the memory 3. 2

Although the calibration curve information 32b of expression (2) is generated using the FDP/DD ratio of each calibrator registered in the memory 32, it also may be generated using the DD concentration of each calibrator registered in the memory 32. When the DD concentration of each calibrator is registered in advance in the memory 32, the processing device 30 can calculate the FDP/DD ratio from the DD concentration registered in the memory 32 and the FDP concentration obtained in the FDP measurement. The processing device 30 can generate the calibration curve information 32b as shown in expression (2) using the calculated FDP/DD ratio.

6. Blood Sample Analysis Example 6.1 FDP Measurement

Samples of commercially available frozen plasma samples (sample-1 to sample-31) and each of the samples for FDP measurement were mixed to prepare 31 analysis measurement samples. FDP measurement kit/Rias Auto P-FDP reagent manufactured by Sysmex Corporation was used for preparing the measurement sample. The FDP concentration was obtained by FDP measurement of each analytical measurement sample by the blood analyzer 10.

Figures 10A, 10B:
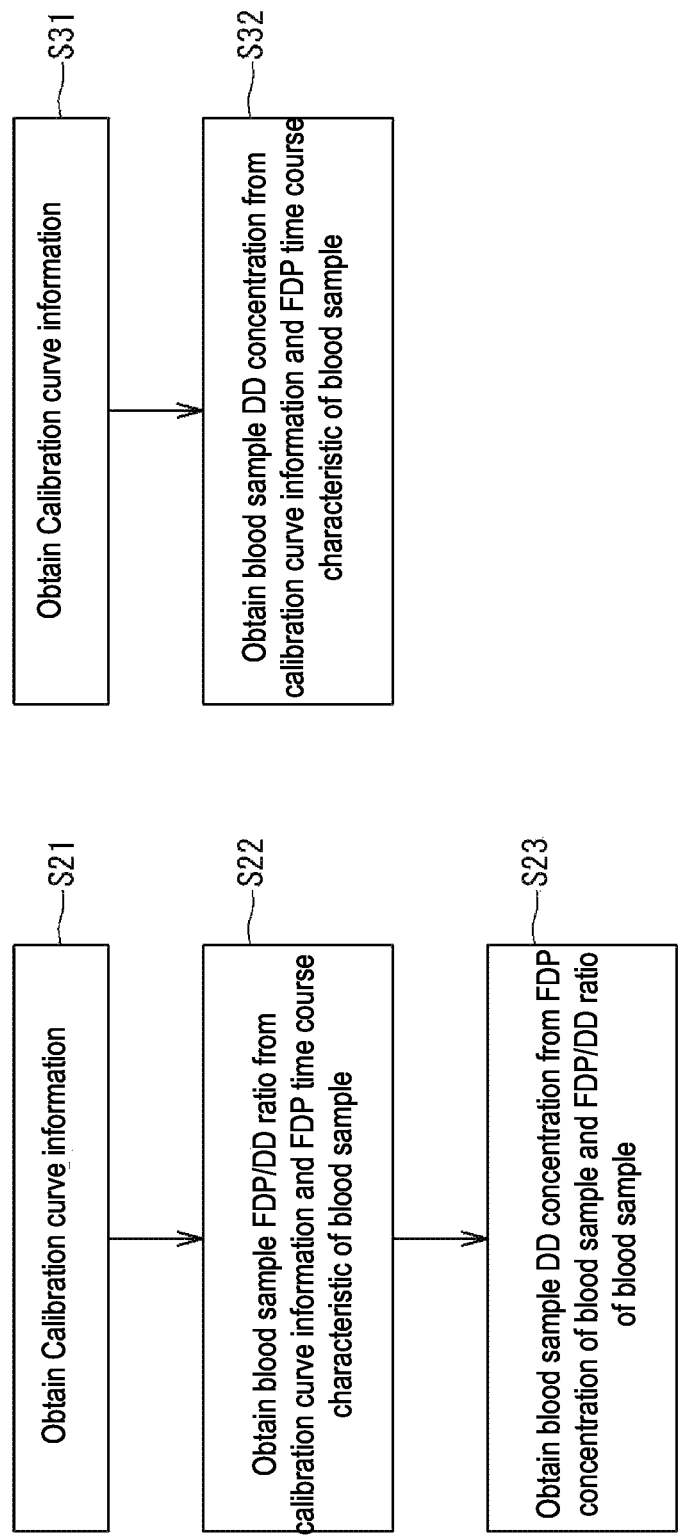
FIGS. 10A and 10B are flow charts of the analysis step.

FIG. 10 shows details of the analysis step of step S14 in FIG. 6. In step S21 of FIG. 10A, the processing device 30 acquires the calibration curve information (expression (2)) registered in the memory 32. In step S22, the processing device 30 calculates the FDP/DD ratio estimate value from the convex area surface area per FDP unit concentration using the calibration curve information (expression (2). In step S23, the processing device 30 calculated the estimated DD concentration from the calculated FDP/DD ratio, and the FDP concentration obtained by FDP measurement. The results are shown in Table 4.

Note that FIG. 10B shows an analysis step when the calibration curve information 32b is information for obtaining the DD concentration. In step S31 of FIG. 10B, the processing device 30 acquires the calibration curve information registered in the memory 32. In step S32, the processing device 30 calculates the DD concentration from the convex area surface area per FDP unit concentration using the calibration curve information.

6.2 DD Measurement

Samples of commercially available frozen plasma samples (sample-1 to sample-31) and DD measurement reagent were mixed to prepare 31 DD measurement samples. A D-dimer measurement kit/Rias Auto D-dimerneo manufactured by Sysmex Corporation was used. The DD measurement sample was subjected to DD measurement with the blood analyzer 10 to obtain DD measured concentration. The results are shown in Table 4.

TABLE 4

|  | FDP concentration (µg/mL) | Concave area surface area (mOD × sec) | Convex surface area per FDP unit concentration | Estimated FDP/DD ratio | Estimated DD concentration (µg/mL) | Actual DD concentration (µg/mL) |
| --- | --- | --- | --- | --- | --- | --- |
| Sample-1 | 102.4 | 12967 | 127 | 3.6 | 28.6 | 34.1 |
| Sample-2 | 101.6 | 13150 | 129 | 3.5 | 29.2 | 35.4 |
| Sample-3 | 99.5 | 13228 | 133 | 3.4 | 29.6 | 36.6 |
| Sample-4 | 70.2 | 15546 | 221 | 1.4 | 49.9 | 43.1 |
| Sample-5 | 68.7 | 14657 | 213 | 1.5 | 45.1 | 42.1 |
| Sample-6 | 67.0 | 6108 | 91 | 5.1 | 13.2 | 22.4 |
| Sample-7 | 54.0 | 11044 | 205 | 1.7 | 32.5 | 26.9 |
| Sample-8 | 45.2 | 7902 | 175 | 2.2 | 20.3 | 26.0 |
| Sample-9 | 45.2 | 12415 | 275 | 0.8 | 54.3 | 35.4 |
| Sample-10 | 44.6 | 11191 | 251 | 1.1 | 42.4 | 34.1 |
| Sample-11 | 42.9 | 12147 | 283 | 0.8 | 56.0 | 33.6 |
| Sample-12 | 42.3 | 10907 | 258 | 1.0 | 43.1 | 33.7 |
| Sample-13 | 35.8 | 4643 | 130 | 3.5 | 10.3 | 14.4 |
| Sample-14 | 28.1 | 5637 | 201 | 1.7 | 16.3 | 12.3 |
| Sample-15 | 24.6 | 1467 | 60 | 6.9 | 3.6 | 2.8 |
| Sample-16 | 24.4 | 4321 | 177 | 2.2 | 11.2 | 12.1 |
| Sample-17 | 22.5 | 4262 | 189 | 1.9 | 11.7 | 14.9 |
| Sample-18 | 21.2 | 2604 | 123 | 3.7 | 5.7 | 5.1 |
| Sample-19 | 20.9 | 4077 | 195 | 1.8 | 11.5 | 10.0 |
| Sample-20 | 19.4 | 3754 | 193 | 1.9 | 10.5 | 8.2 |
| Sample-21 | 18.9 | 3556 | 188 | 2.0 | 9.7 | 11.4 |
| Sample-22 | 17.7 | 3694 | 209 | 1.6 | 11.1 | 10.3 |
| Sample-23 | 17.1 | 2238 | 131 | 3.4 | 5.0 | 5.3 |
| Sample-24 | 16.6 | 2366 | 143 | 3.1 | 5.4 | 6.8 |
| Sample-25 | 16.5 | 2227 | 135 | 3.3 | 5.0 | 4.0 |
| Sample-26 | 14.0 | 2790 | 199 | 1.7 | 8.0 | 6.9 |
| Sample-27 | 13.9 | 2684 | 193 | 1.9 | 7.5 | 6.5 |
| Sample-28 | 11.5 | 1778 | 155 | 2.7 | 4.2 | 6.0 |
| Sample-29 | 7.2 | 1087 | 151 | 2.8 | 2.6 | 2.2 |
| Sample-30 | 6.6 | 1133 | 172 | 2.3 | 2.9 | 2.9 |
| Sample-31 | 6.5 | 1156 | 178 | 2.2 | 3.0 | 2.6 |

Further, the blood analyzer 10 obtained the convex area surface area which is a time course characteristic as FDP calculation data, and obtained the convex area surface area per FDP unit concentration. The results are shown in Table 4.

Figure 11:
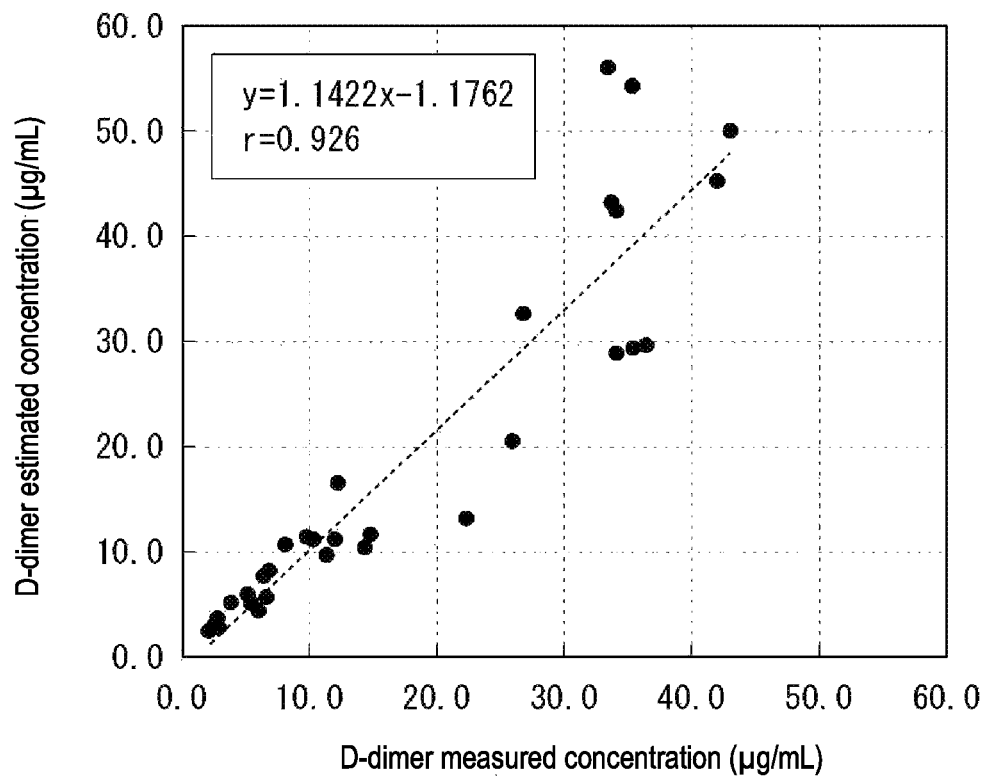
FIG. 11 is a correlation diagram between DD measured concentration and DD estimated concentration.

FIG. 11 is a correlation diagram in which 31 samples (sample-1 to sample-31) of frozen plasma are plotted with the DD estimated concentration obtained on the vertical axis and the DD actually measured concentration as the horizontal axis. In FIG. 11, the correlation coefficient (r) is 0.926, and a high correlation between DD estimated concentration and measured DD concentration is recognized.

6.3 Determination of Fibrinolysis-Enhanced State

Generally, in the determination of fibrinolysis-enhanced DIC, FDP concentration and FDP/DD ratio are used as threshold values. The determination of the fibrinolysis-enhanced DIC includes, for example, comparing the FDP concentration of the sample with the FDP concentration reference value and comparing the FDP/DD ratio of the sample with the FDP/DD ratio reference value. The FDP concentration reference value is, for example, 80 μg/mL. The FDP/DD ratio reference value is, for example, a value in the range of 3 to 5. For example, fibrinolysis-enhanced DIC is determined when the FDP concentration of the sample is equal to or higher than the FDP concentration reference value and the FDP/DD ratio of the sample is equal to or higher than the FDP/DD ratio reference value.

The processing device 30 of the embodiment determines fibrinolysis-enhanced DIC using the FDP/DD ratio estimate value acquired in the analysis step (step S14) and the FDP actual measurement concentration. Generally, in order to make a determination of fibrinolysis-enhanced DIC (determination of enhanced fibrinolysis state) using FDP concentration and FDP/DD ratio, FDP measurement and DD measurement must be performed to obtain the FDP/DD ratio. The DD measurement is performed using the DD measurement reagent, and it is necessary to perform the DD measurement separately from the FDP measurement. If both measurements of FDP measurement and DD measurement are performed, the cost will be high. On the other hand, since the FDP/DD ratio estimate value is obtained from the measurement result of the FDP measurement in the embodiment, it is possible to omit the DD measurement.

7. Sample Analysis Result Screen

The processing device 30 causes the display unit 33 to display the result display screen 100 shown in FIG. 12 in step S15 of FIG. 6. The result display screen 100 has a display area of a fibrinolysis-enhanced flag 101, an FDP/DD estimation value 102, and a DD estimation value 103, in addition to FDP measurement values indicating measurement date and time, sample number, and FDP concentration, for each sample. The fibrinolysis-enhanced flag 101 indicates whether the sample is determined to be in a fibrinolysis-enhanced state. For samples determined to be in the fibrinolysis-enhanced state, for example, "enhanced fibrinolysis" is indicated in the region of the fibrinolysis-enhanced flag 101.

The region of the FDP/DD estimate value 102 displays the estimated value of the FDP/DD ratio, and the region of the DD estimate value 103 displays the estimated value of the DD concentration.

8. Supplement

In the above embodiment, the DD concentration is estimated and the fibrinolysis-enhanced state determination is performed by FDP measurement without DD measurement, but further DD measurement may be performed. For example, as a primary screening, after determination of fibrinolysis-enhanced state by FDP measurement without performing DD measurement, DD measurement is performed as a secondary test to determine FDP/D-dimer ratio.

Further, when the value of DD concentration obtained by DD measurement is an abnormal value, whether the value of DD concentration is an abnormal value may be confirmed using the estimate value of DD concentration obtained by FDP measurement. As described above, DD measurement may be performed in the practice of the present invention.

What is claimed is:

1. A blood analyzing method comprising:
    performing optical measurement on a first calibration measurement sample prepared from a fibrin/fibrinogen degradation product (FDP) measurement reagent and a first calibrator, wherein the first calibrator contains D dimer (DD) at a first value of a ratio of FDP content to DD content (FDP/DD ratio);
    acquiring first calculation data including a first shape characteristic of a first time course curve representing a temporal change in first optical information obtained by the optical measurement on the first calibration measurement sample;
    performing optical measurement on a second calibration measurement sample prepared from the FDP measurement reagent and a second calibrator, wherein the second calibrator contains DD at a second value of FDP/DD ratio that is different from the first value;
    acquiring second calculation data including a second shape characteristic of a second time course curve representing a temporal change in second optical information obtained by the optical measurement on the second calibration measurement sample;
    acquiring calibration curve information based on the first calculation data, the second calculation data, the first value, and the second value;
    performing optical measurement on an analysis measurement sample prepared from a blood sample and the FDP measurement reagent;
    acquiring analysis calculation data of FDP content based on a temporal change in third optical information obtained by the optical measurement on the analysis measurement sample; and
    acquiring analysis calculation data of DD content based on the analysis calculation data of FDP content and the calibration curve information.

2. The method of claim 1, wherein
    the first calculation data represents a degree of curvature of the first time course curve, and
    the second calculation data represents a degree of curvature of the second time course curve.

3. The method of claim 1, wherein the analysis calculation data of FDP content comprises a FDP concentration of the blood sample and a third shape characteristic of a third time course curve representing the temporal change in the third optical.

4. The method of claim 1, further comprising:
    comparing a FDP/DD ratio of the blood sample with a FDP/DD ratio reference value for analysis of the blood sample, wherein at least one of the first value and the second value is a value equal to or within a predetermined range of the reference value.

* * * * *

UNITED STATES PATENT AND TRADEMARK OFFICE
CERTIFICATE OF CORRECTION

PATENT NO. : 11,162,957 B2  
APPLICATION NO. : 15/622702  
DATED : November 2, 2021  
INVENTOR(S) : Junki Hayasaki Page 1 of 1

It is certified that error appears in the above-identified patent and that said Letters Patent is hereby corrected as shown below:

In the Claims

Column 24, Claim 3, Line 53 - after the word optical, please insert --information--

Signed and Sealed this  
Eleventh Day of January, 2022

Drew Hirshfeld  
*Performing the Functions and Duties of the*  
*Under Secretary of Commerce for Intellectual Property and*  
*Director of the United States Patent and Trademark Office*